US012746096B2

(12) United States Patent
Reichenbach et al.

(10) Patent No.: US 12,746,096 B2
(45) Date of Patent: Sep. 29, 2026

(54) GROSS POSITIONING DEVICE AND RELATED SYSTEMS AND METHODS

(71) Applicant: Board of Regents of the University of Nebraska, Lincoln, NE (US)

(72) Inventors: Mark Reichenbach, Lincoln, NE (US); Shane Farritor, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 18/826,601

(22) Filed: Sep. 6, 2024

(65) Prior Publication Data

US 2024/0423753 A1 Dec. 26, 2024

Related U.S. Application Data

(63) Continuation of application No. 18/482,959, filed on Oct. 9, 2023, now Pat. No. 12,109,079, which is a continuation of application No. 17/838,883, filed on Jun. 13, 2022, now Pat. No. 11,813,124, which is a (Continued)

(51) Int. Cl.

*A61B 90/50* (2016.01)
*A61B 1/00* (2006.01)
*A61B 17/02* (2006.01)
*A61B 34/00* (2016.01)

(Continued)

(52) U.S. Cl.

CPC .......... *A61B 90/50* (2016.02); *A61B 1/00149* (2013.01); *A61B 17/0206* (2013.01); *A61B 34/30* (2016.02); *A61B 34/73* (2016.02); *A61B 2017/00477* (2013.01); *A61B 2034/302* (2016.02); *A61B 2218/002* (2013.01); *A61B 2218/007* (2013.01)

(58) Field of Classification Search

None

See application file for complete search history.

(56) References Cited

U.S. PATENT DOCUMENTS

| | | | |
|---|---|---|---|
| 3,870,264 | A | 3/1975 | Robinson |
| 3,989,952 | A | 11/1976 | Hohmann |
| 4,246,661 | A | 1/1981 | Pinson |

(Continued)

FOREIGN PATENT DOCUMENTS

| | | | |
|---|---|---|---|
| CN | 102821918 | A | 12/2012 |
| CN | 105979902 | A | 9/2016 |

(Continued)

OTHER PUBLICATIONS

Southern Surgeons Club (1991), "A prospective analysis of 1518 laparoscopic cholecystectomies," N. Eng. 1 Med. 324 (16): 1073-1078.

(Continued)

*Primary Examiner* — Vicky A Johnson

(74) *Attorney, Agent, or Firm* — Fredrikson & Byron, P.A.

(57) ABSTRACT

Disclosed herein are gross positioning systems for use with robotic surgical devices to provide gross positioning of the robotic surgical devices. The gross positioning systems have a base, a first arm link operably coupled to the base, a second arm link operably coupled to the first arm link, a third arm link operably coupled to the second arm link, and a slidable coupling component slidably coupled to the third arm link.

19 Claims, 10 Drawing Sheets

Related U.S. Application Data continuation of application No. 15/821,169, filed on Nov. 22, 2017, now Pat. No. 11,357,595.

(60) Provisional application No. 62/425,149, filed on Nov. 22, 2016.

(51) Int. Cl.
*A61B 34/30* (2016.01)
*A61B 17/00* (2006.01)

(56) References Cited

U.S. PATENT DOCUMENTS

| | | | |
|---|---|---|---|
| 4,258,716 | A | 3/1981 | Sutherland |
| 4,278,077 | A | 7/1981 | Mizumoto |
| 4,538,594 | A | 9/1985 | Boebel et al. |
| 4,568,311 | A | 2/1986 | Miyake |
| 4,623,183 | A | 11/1986 | Aomori |
| 4,736,645 | A | 4/1988 | Zimmer |
| 4,771,652 | A | 9/1988 | Zimmer |
| 4,852,391 | A | 8/1989 | Ruch et al. |
| 4,896,015 | A | 1/1990 | Taboada et al. |
| 4,897,014 | A | 1/1990 | Tietze |
| 4,922,755 | A | 5/1990 | Oshiro et al. |
| 4,922,782 | A | 5/1990 | Kawai |
| 4,990,050 | A | 2/1991 | Tsuge et al. |
| 5,007,550 | A | 4/1991 | Avot |
| 5,019,968 | A | 5/1991 | Wang et al. |
| 5,030,365 | A | 7/1991 | Christensen et al. |
| 5,063,095 | A | 11/1991 | Kitagawa et al. |
| 5,066,090 | A | 11/1991 | Mayerhofer et al. |
| 5,108,140 | A | 4/1992 | Bartholet |
| 5,139,563 | A | 8/1992 | Astles et al. |
| 5,172,639 | A | 12/1992 | Wiesman et al. |
| 5,176,649 | A | 1/1993 | Wakabayashi |
| 5,178,032 | A | 1/1993 | Zona et al. |
| 5,187,796 | A | 2/1993 | Wang et al. |
| 5,195,388 | A | 3/1993 | Zona et al. |
| 5,201,325 | A | 4/1993 | Mcewen et al. |
| 5,217,003 | A | 6/1993 | Wilk |
| 5,263,382 | A | 11/1993 | Brooks et al. |
| 5,271,384 | A | 12/1993 | Mcewen et al. |
| 5,284,096 | A | 2/1994 | Pelrine et al. |
| 5,297,443 | A | 3/1994 | Wentz |
| 5,297,536 | A | 3/1994 | Wilk |
| 5,304,899 | A | 4/1994 | Sasaki et al. |
| 5,307,447 | A | 4/1994 | Asano et al. |
| 5,353,807 | A | 10/1994 | Demarco |
| 5,363,935 | A | 11/1994 | Schempf et al. |
| 5,382,885 | A | 1/1995 | Salcudean et al. |
| 5,388,528 | A | 2/1995 | Pelrine et al. |
| 5,436,542 | A | 7/1995 | Petelin et al. |
| 5,441,494 | A | 8/1995 | Ortiz |
| 5,450,104 | A | 9/1995 | Kisa et al. |
| 5,451,027 | A | 9/1995 | Mchenry |
| 5,454,758 | A | 10/1995 | Tophinke et al. |
| 5,458,131 | A | 10/1995 | Wilk |
| 5,458,583 | A | 10/1995 | Mcneely et al. |
| 5,458,598 | A | 10/1995 | Feinberg et al. |
| 5,459,926 | A | 10/1995 | Perea |
| 5,463,361 | A | 10/1995 | Allen |
| 5,468,203 | A | 11/1995 | Okonkwo |
| 5,468,265 | A | 11/1995 | Adams |
| 5,470,236 | A | 11/1995 | Wissler |
| 5,471,515 | A | 11/1995 | Fossum et al. |
| 5,491,691 | A | 2/1996 | Shtayer et al. |
| 5,491,701 | A | 2/1996 | Zook |
| 5,497,651 | A | 3/1996 | Matter et al. |
| 5,515,478 | A | 5/1996 | Wang |
| 5,524,180 | A | 6/1996 | Wang et al. |
| 5,553,198 | A | 9/1996 | Wang et al. |
| 5,562,448 | A | 10/1996 | Mushabac |
| 5,588,442 | A | 12/1996 | Scovil et al. |
| 5,620,417 | A | 4/1997 | Jang et al. |
| 5,623,582 | A | 4/1997 | Rosenberg |
| 5,624,380 | A | 4/1997 | Shinji et al. |
| 5,624,398 | A | 4/1997 | Smith et al. |
| 5,632,761 | A | 5/1997 | Smith et al. |
| 5,645,520 | A | 7/1997 | Nakamura et al. |
| 5,657,429 | A | 8/1997 | Wang et al. |
| 5,657,584 | A | 8/1997 | Hamlin |
| 5,672,168 | A | 9/1997 | De La Torre et al. |
| 5,674,030 | A | 10/1997 | Sigel |
| 5,728,599 | A | 3/1998 | Rostoker et al. |
| 5,736,821 | A | 4/1998 | Suyama |
| 5,754,741 | A | 5/1998 | Wang et al. |
| 5,762,458 | A | 6/1998 | Wang et al. |
| 5,769,640 | A | 6/1998 | Jacobus et al. |
| 5,791,231 | A | 8/1998 | Cohn et al. |
| 5,792,135 | A | 8/1998 | Madhani et al. |
| 5,792,663 | A | 8/1998 | Fry et al. |
| 5,797,538 | A | 8/1998 | Heaton et al. |
| 5,797,900 | A | 8/1998 | Madhani et al. |
| 5,807,377 | A | 9/1998 | Madhani et al. |
| 5,808,665 | A | 9/1998 | Green |
| 5,815,640 | A | 9/1998 | Wang et al. |
| 5,825,982 | A | 10/1998 | Wright et al. |
| 5,841,950 | A | 11/1998 | Wang et al. |
| 5,845,646 | A | 12/1998 | Lemelson |
| 5,855,583 | A | 1/1999 | Wang et al. |
| 5,876,325 | A | 3/1999 | Mizuno et al. |
| 5,878,193 | A | 3/1999 | Wang et al. |
| 5,878,783 | A | 3/1999 | Smart |
| 5,895,417 | A | 4/1999 | Pomeranz et al. |
| 5,906,591 | A | 5/1999 | Dario et al. |
| 5,907,664 | A | 5/1999 | Wang et al. |
| 5,910,129 | A | 6/1999 | Koblish et al. |
| 5,911,036 | A | 6/1999 | Wright et al. |
| 5,971,976 | A | 10/1999 | Wang et al. |
| 5,993,467 | A | 11/1999 | Yoon |
| 6,001,108 | A | 12/1999 | Wang et al. |
| 6,007,550 | A | 12/1999 | Wang et al. |
| 6,030,365 | A | 2/2000 | Laufer |
| 6,031,371 | A | 2/2000 | Smart |
| 6,058,323 | A | 5/2000 | Lemelson |
| 6,063,095 | A | 5/2000 | Wang et al. |
| 6,066,090 | A | 5/2000 | Yoon |
| 6,086,529 | A | 7/2000 | Arndt |
| 6,102,850 | A | 8/2000 | Wang et al. |
| 6,107,795 | A | 8/2000 | Smart |
| 6,132,368 | A | 10/2000 | Cooper |
| 6,132,441 | A | 10/2000 | Grace |
| 6,139,563 | A | 10/2000 | Cosgrove, III et al. |
| 6,156,006 | A | 12/2000 | Brosens et al. |
| 6,159,146 | A | 12/2000 | El Gazayerli |
| 6,162,171 | A | 12/2000 | Ng et al. |
| D438,617 | S | 3/2001 | Cooper et al. |
| 6,206,903 | B1 | 3/2001 | Ramans |
| D441,076 | S | 4/2001 | Cooper et al. |
| 6,223,100 | B1 | 4/2001 | Green |
| D441,862 | S | 5/2001 | Cooper et al. |
| 6,238,415 | B1 | 5/2001 | Sepetka et al. |
| 6,240,312 | B1 | 5/2001 | Alfano et al. |
| 6,241,730 | B1 | 6/2001 | Alby |
| 6,244,809 | B1 | 6/2001 | Wang et al. |
| 6,246,200 | B1 | 6/2001 | Blumenkranz et al. |
| D444,555 | S | 7/2001 | Cooper et al. |
| 6,286,514 | B1 | 9/2001 | Lemelson |
| 6,292,678 | B1 | 9/2001 | Hall et al. |
| 6,293,282 | B1 | 9/2001 | Lemelson |
| 6,296,635 | B1 | 10/2001 | Smith et al. |
| 6,307,447 | B1 | 10/2001 | Barber et al. |
| 6,309,397 | B1 | 10/2001 | Julian et al. |
| 6,309,403 | B1 | 10/2001 | Minor et al. |
| 6,312,435 | B1 | 11/2001 | Wallace et al. |
| 6,321,106 | B1 | 11/2001 | Lemelson |
| 6,327,492 | B1 | 12/2001 | Lemelson |
| 6,331,181 | B1 | 12/2001 | Tierney et al. |
| 6,346,072 | B1 | 2/2002 | Cooper |
| 6,352,503 | B1 | 3/2002 | Matsui et al. |
| 6,364,888 | B1 | 4/2002 | Niemeyer et al. |
| 6,371,952 | B1 | 4/2002 | Madhani et al. |
| 6,382,885 | B2 | 5/2002 | Isaksson |
| 6,388,528 | B1 | 5/2002 | Buer et al. |

(56) References Cited

U.S. PATENT DOCUMENTS

| | | | |
|---|---|---|---|
| 6,394,998 | B1 | 5/2002 | Wallace et al. |
| 6,398,726 | B1 | 6/2002 | Ramans et al. |
| 6,400,980 | B1 | 6/2002 | Lemelson |
| 6,408,224 | B1 | 6/2002 | Okamoto et al. |
| 6,424,885 | B1 | 7/2002 | Niemeyer et al. |
| 6,432,112 | B2 | 8/2002 | Brock et al. |
| 6,436,107 | B1 | 8/2002 | Wang et al. |
| 6,441,577 | B2 | 8/2002 | Blumenkranz et al. |
| 6,450,104 | B1 | 9/2002 | Grant et al. |
| 6,451,027 | B1 | 9/2002 | Cooper et al. |
| 6,454,758 | B1 | 9/2002 | Thompson et al. |
| 6,458,131 | B1 | 10/2002 | Ray |
| 6,458,583 | B1 | 10/2002 | Bruhn et al. |
| 6,459,926 | B1 | 10/2002 | Nowlin et al. |
| 6,463,361 | B1 | 10/2002 | Wang et al. |
| 6,468,203 | B2 | 10/2002 | Belson |
| 6,468,265 | B1 | 10/2002 | Evans et al. |
| 6,470,236 | B2 | 10/2002 | Ohtsuki |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,496,099 | B2 | 12/2002 | Wang et al. |
| 6,497,651 | B1 | 12/2002 | Kan et al. |
| 6,508,413 | B2 | 1/2003 | Bauer et al. |
| 6,512,345 | B2 | 1/2003 | Borenstein et al. |
| 6,515,478 | B1 | 2/2003 | Wicklow et al. |
| 6,522,906 | B1 | 2/2003 | Salisbury et al. |
| 6,544,276 | B1 | 4/2003 | Azizi |
| 6,548,982 | B1 | 4/2003 | Papanikolopoulos et al. |
| 6,554,790 | B1 | 4/2003 | Moll |
| 6,562,448 | B1 | 5/2003 | Chamberlain et al. |
| 6,565,554 | B1 | 5/2003 | Niemeyer |
| 6,574,355 | B2 | 6/2003 | Green |
| 6,587,750 | B2 | 7/2003 | Gerbi et al. |
| 6,588,442 | B2 | 7/2003 | Babin |
| 6,591,239 | B1 | 7/2003 | Mccall et al. |
| 6,594,552 | B1 | 7/2003 | Nowlin et al. |
| 6,610,007 | B2 | 8/2003 | Belson et al. |
| 6,620,173 | B2 | 9/2003 | Gerbi et al. |
| 6,624,398 | B2 | 9/2003 | Sherrill et al. |
| 6,632,761 | B1 | 10/2003 | Ushita et al. |
| 6,642,836 | B1 | 11/2003 | Wang et al. |
| 6,645,196 | B1 | 11/2003 | Nixon et al. |
| 6,646,541 | B1 | 11/2003 | Wang et al. |
| 6,648,814 | B2 | 11/2003 | Kim et al. |
| 6,657,584 | B2 | 12/2003 | Cavallaro et al. |
| 6,659,939 | B2 | 12/2003 | Moll et al. |
| 6,661,571 | B1 | 12/2003 | Shioda et al. |
| 6,671,581 | B2 | 12/2003 | Niemeyer et al. |
| 6,676,684 | B1 | 1/2004 | Morley et al. |
| 6,684,129 | B2 | 1/2004 | Salisbury et al. |
| 6,685,648 | B2 | 2/2004 | Flaherty et al. |
| 6,685,698 | B2 | 2/2004 | Morley et al. |
| 6,687,571 | B1 | 2/2004 | Byrne et al. |
| 6,692,485 | B1 | 2/2004 | Brock et al. |
| 6,699,177 | B1 | 3/2004 | Wang et al. |
| 6,699,235 | B2 | 3/2004 | Wallace et al. |
| 6,702,734 | B2 | 3/2004 | Kim et al. |
| 6,702,805 | B1 | 3/2004 | Stuart |
| 6,714,839 | B2 | 3/2004 | Salisbury et al. |
| 6,714,841 | B1 | 3/2004 | Wright et al. |
| 6,719,684 | B2 | 4/2004 | Kim et al. |
| 6,720,988 | B1 | 4/2004 | Gere et al. |
| 6,726,699 | B1 | 4/2004 | Wright et al. |
| 6,728,599 | B2 | 4/2004 | Wang et al. |
| 6,730,021 | B2 | 5/2004 | Vassiliades et al. |
| 6,731,988 | B1 | 5/2004 | Green |
| 6,736,821 | B2 | 5/2004 | Squires et al. |
| 6,746,443 | B1 | 6/2004 | Morley et al. |
| 6,754,741 | B2 | 6/2004 | Alexander et al. |
| 6,764,441 | B2 | 7/2004 | Chiel et al. |
| 6,764,445 | B2 | 7/2004 | Ramans et al. |
| 6,766,204 | B2 | 7/2004 | Niemeyer et al. |
| 6,770,081 | B1 | 8/2004 | Cooper et al. |
| 6,774,597 | B1 | 8/2004 | Borenstein |
| 6,776,165 | B2 | 8/2004 | Jin |
| 6,780,184 | B2 | 8/2004 | Tanrisever |
| 6,783,524 | B2 | 8/2004 | Anderson et al. |
| 6,785,593 | B2 | 8/2004 | Wang et al. |
| 6,788,018 | B1 | 9/2004 | Blumenkranz |
| 6,791,231 | B2 | 9/2004 | Chang |
| 6,792,135 | B1 | 9/2004 | Toyama |
| 6,792,663 | B2 | 9/2004 | Krzyzanowski |
| 6,793,653 | B2 | 9/2004 | Sanchez et al. |
| 6,799,065 | B1 | 9/2004 | Niemeyer |
| 6,799,088 | B2 | 9/2004 | Wang et al. |
| 6,801,325 | B2 | 10/2004 | Farr et al. |
| 6,804,581 | B2 | 10/2004 | Wang et al. |
| 6,810,281 | B2 | 10/2004 | Brock et al. |
| 6,815,640 | B1 | 11/2004 | Spear et al. |
| 6,817,972 | B2 | 11/2004 | Snow |
| 6,817,974 | B2 | 11/2004 | Cooper et al. |
| 6,817,975 | B1 | 11/2004 | Farr et al. |
| 6,820,653 | B1 | 11/2004 | Schempf et al. |
| 6,824,508 | B2 | 11/2004 | Kim et al. |
| 6,824,510 | B2 | 11/2004 | Kim et al. |
| 6,832,988 | B2 | 12/2004 | Sproul |
| 6,832,996 | B2 | 12/2004 | Woloszko et al. |
| 6,836,703 | B2 | 12/2004 | Wang et al. |
| 6,837,846 | B2 | 1/2005 | Jaffe et al. |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,845,646 | B2 | 1/2005 | Goto |
| 6,852,107 | B2 | 2/2005 | Wang et al. |
| 6,855,583 | B1 | 2/2005 | Krivokapic et al. |
| 6,858,003 | B2 | 2/2005 | Evans et al. |
| 6,860,346 | B2 | 3/2005 | Burt et al. |
| 6,860,877 | B1 | 3/2005 | Sanchez et al. |
| 6,866,671 | B2 | 3/2005 | Tierney et al. |
| 6,870,343 | B2 | 3/2005 | Borenstein et al. |
| 6,871,117 | B2 | 3/2005 | Wang et al. |
| 6,871,563 | B2 | 3/2005 | Choset et al. |
| 6,878,783 | B2 | 4/2005 | Yeager et al. |
| 6,879,880 | B2 | 4/2005 | Nowlin et al. |
| 6,892,112 | B2 | 5/2005 | Wang et al. |
| 6,895,417 | B2 | 5/2005 | Obara et al. |
| 6,899,705 | B2 | 5/2005 | Niemeyer |
| 6,902,560 | B1 | 6/2005 | Morley et al. |
| 6,905,460 | B2 | 6/2005 | Wang et al. |
| 6,905,491 | B1 | 6/2005 | Wang et al. |
| 6,911,036 | B2 | 6/2005 | Douk et al. |
| 6,911,916 | B1 | 6/2005 | Wang et al. |
| 6,917,176 | B2 | 7/2005 | Schempf et al. |
| 6,933,695 | B2 | 8/2005 | Blumenkranz |
| 6,936,001 | B1 | 8/2005 | Snow |
| 6,936,003 | B2 | 8/2005 | Iddan |
| 6,936,042 | B2 | 8/2005 | Wallace et al. |
| 6,943,663 | B2 | 9/2005 | Wang et al. |
| 6,949,096 | B2 | 9/2005 | Davison et al. |
| 6,951,535 | B2 | 10/2005 | Ghodoussi et al. |
| 6,965,812 | B2 | 11/2005 | Wang et al. |
| 6,974,411 | B2 | 12/2005 | Belson |
| 6,974,449 | B2 | 12/2005 | Niemeyer |
| 6,979,423 | B2 | 12/2005 | Moll |
| 6,984,203 | B2 | 1/2006 | Tartaglia et al. |
| 6,984,205 | B2 | 1/2006 | Gazdzinski |
| 6,991,627 | B2 | 1/2006 | Madhani et al. |
| 6,993,413 | B2 | 1/2006 | Sunaoshi |
| 6,994,703 | B2 | 2/2006 | Wang et al. |
| 6,994,708 | B2 | 2/2006 | Manzo |
| 6,997,908 | B2 | 2/2006 | Carrillo, Jr. et al. |
| 7,025,064 | B2 | 4/2006 | Wang et al. |
| 7,027,892 | B2 | 4/2006 | Wang et al. |
| 7,033,344 | B2 | 4/2006 | Imran |
| 7,039,453 | B2 | 5/2006 | Mullick et al. |
| 7,042,184 | B2 | 5/2006 | Oleynikov et al. |
| 7,048,745 | B2 | 5/2006 | Tierney et al. |
| 7,053,752 | B2 | 5/2006 | Wang et al. |
| 7,063,682 | B1 | 6/2006 | Whayne et al. |
| 7,066,879 | B2 | 6/2006 | Fowler et al. |
| 7,066,926 | B2 | 6/2006 | Wallace et al. |
| 7,074,179 | B2 | 7/2006 | Wang et al. |
| 7,077,446 | B2 | 7/2006 | Kameda et al. |

(56) References Cited

U.S. PATENT DOCUMENTS

| | | | |
|---|---|---|---|
| 7,083,571 | B2 | 8/2006 | Wang et al. |
| 7,083,615 | B2 | 8/2006 | Peterson et al. |
| 7,087,049 | B2 | 8/2006 | Nowlin et al. |
| 7,090,683 | B2 | 8/2006 | Brock et al. |
| 7,097,640 | B2 | 8/2006 | Wang et al. |
| 7,105,000 | B2 | 9/2006 | Mcbrayer |
| 7,107,090 | B2 | 9/2006 | Salisbury, Jr. et al. |
| 7,109,678 | B2 | 9/2006 | Kraus et al. |
| 7,118,582 | B1 | 10/2006 | Wang et al. |
| 7,121,781 | B2 | 10/2006 | Sanchez |
| 7,125,403 | B2 | 10/2006 | Julian et al. |
| 7,126,303 | B2 | 10/2006 | Farritor et al. |
| 7,147,650 | B2 | 12/2006 | Lee |
| 7,155,315 | B2 | 12/2006 | Niemeyer et al. |
| 7,166,113 | B2 | 1/2007 | Arambula et al. |
| 7,169,141 | B2 | 1/2007 | Brock et al. |
| 7,182,025 | B2 | 2/2007 | Ghorbel et al. |
| 7,182,089 | B2 | 2/2007 | Ries |
| 7,199,545 | B2 | 4/2007 | Oleynikov et al. |
| 7,206,626 | B2 | 4/2007 | Quaid, III |
| 7,206,627 | B2 | 4/2007 | Abovitz et al. |
| 7,210,364 | B2 | 5/2007 | Ghorbel et al. |
| 7,214,230 | B2 | 5/2007 | Brock et al. |
| 7,217,240 | B2 | 5/2007 | Snow |
| 7,239,940 | B2 | 7/2007 | Wang et al. |
| 7,250,028 | B2 | 7/2007 | Julian et al. |
| 7,259,652 | B2 | 8/2007 | Wang et al. |
| 7,273,488 | B2 | 9/2007 | Nakamura et al. |
| 7,311,107 | B2 | 12/2007 | Harel et al. |
| 7,339,341 | B2 | 3/2008 | Oleynikov et al. |
| 7,372,229 | B2 | 5/2008 | Farritor et al. |
| 7,447,537 | B1 | 11/2008 | Funda et al. |
| 7,492,116 | B2 | 2/2009 | Oleynikov et al. |
| 7,566,300 | B2 | 7/2009 | Devierre et al. |
| 7,574,250 | B2 | 8/2009 | Niemeyer |
| 7,588,537 | B2 | 9/2009 | Bass |
| 7,637,905 | B2 | 12/2009 | Saadat et al. |
| 7,645,230 | B2 | 1/2010 | Mikkaichi et al. |
| 7,655,004 | B2 | 2/2010 | Long |
| 7,670,329 | B2 | 3/2010 | Flaherty et al. |
| 7,672,168 | B2 | 3/2010 | Tanaka et al. |
| 7,678,043 | B2 | 3/2010 | Gilad |
| 7,731,727 | B2 | 6/2010 | Sauer |
| 7,762,825 | B2 | 7/2010 | Burbank et al. |
| 7,772,796 | B2 | 8/2010 | Farritor et al. |
| 7,785,251 | B2 | 8/2010 | Wilk |
| 7,785,333 | B2 | 8/2010 | Miyamoto et al. |
| 7,789,825 | B2 | 9/2010 | Nobis et al. |
| 7,794,494 | B2 | 9/2010 | Sahatjian et al. |
| 7,799,088 | B2 | 9/2010 | Geitz |
| 7,865,266 | B2 | 1/2011 | Moll et al. |
| 7,960,935 | B2 | 6/2011 | Farritor et al. |
| 8,021,358 | B2 | 9/2011 | Doyle et al. |
| 8,179,073 | B2 | 5/2012 | Farritor et al. |
| 8,182,469 | B2 | 5/2012 | Anderson et al. |
| 8,231,510 | B2 | 7/2012 | Abdo |
| 8,231,610 | B2 | 7/2012 | Jo et al. |
| 8,353,897 | B2 | 1/2013 | Doyle et al. |
| 8,604,742 | B2 | 12/2013 | Farritor et al. |
| 9,089,353 | B2 | 7/2015 | Farritor et al. |
| 9,649,020 | B2 | 5/2017 | Finlay |
| 11,357,595 | B2 | 6/2022 | Reichenbach et al. |
| 2001/0018591 | A1 | 8/2001 | Brock et al. |
| 2001/0049497 | A1 | 12/2001 | Kalloo et al. |
| 2002/0003173 | A1 | 1/2002 | Bauer et al. |
| 2002/0013601 | A1 | 1/2002 | Nobles et al. |
| 2002/0026186 | A1 | 2/2002 | Woloszko et al. |
| 2002/0038077 | A1 | 3/2002 | De La Torre et al. |
| 2002/0065507 | A1 | 5/2002 | Zadno-Azizi |
| 2002/0091374 | A1 | 7/2002 | Cooper |
| 2002/0103417 | A1 | 8/2002 | Gazdzinski |
| 2002/0111535 | A1 | 8/2002 | Kim et al. |
| 2002/0120254 | A1 | 8/2002 | Julian et al. |
| 2002/0128552 | A1 | 9/2002 | Nowlin et al. |
| 2002/0133174 | A1 | 9/2002 | Charles et al. |
| 2002/0140392 | A1 | 10/2002 | Borenstein et al. |
| 2002/0147487 | A1 | 10/2002 | Sundquist et al. |
| 2002/0151906 | A1 | 10/2002 | Demarais et al. |
| 2002/0156347 | A1 | 10/2002 | Kim et al. |
| 2002/0171385 | A1 | 11/2002 | Kim et al. |
| 2002/0173700 | A1 | 11/2002 | Kim et al. |
| 2002/0190682 | A1 | 12/2002 | Schempf et al. |
| 2003/0020810 | A1 | 1/2003 | Takizawa et al. |
| 2003/0045888 | A1 | 3/2003 | Brock et al. |
| 2003/0065250 | A1 | 4/2003 | Chiel et al. |
| 2003/0089267 | A1 | 5/2003 | Ghorbel et al. |
| 2003/0092964 | A1 | 5/2003 | Kim et al. |
| 2003/0097129 | A1 | 5/2003 | Davison et al. |
| 2003/0100817 | A1 | 5/2003 | Wang et al. |
| 2003/0114731 | A1 | 6/2003 | Cadeddu et al. |
| 2003/0135203 | A1 | 7/2003 | Wang et al. |
| 2003/0139742 | A1 | 7/2003 | Wampler et al. |
| 2003/0144656 | A1 | 7/2003 | Ocel et al. |
| 2003/0159535 | A1 | 8/2003 | Grover et al. |
| 2003/0167000 | A1 | 9/2003 | Mullick et al. |
| 2003/0172871 | A1 | 9/2003 | Scherer |
| 2003/0179308 | A1 | 9/2003 | Zamorano et al. |
| 2003/0181788 | A1 | 9/2003 | Yokoi et al. |
| 2003/0191455 | A1 | 10/2003 | Sanchez et al. |
| 2003/0229268 | A1 | 12/2003 | Uchiyama et al. |
| 2003/0229338 | A1 | 12/2003 | Irion et al. |
| 2003/0230372 | A1 | 12/2003 | Schmidt |
| 2004/0016906 | A1 | 1/2004 | Kondo et al. |
| 2004/0024311 | A1 | 2/2004 | Quaid, III |
| 2004/0034282 | A1 | 2/2004 | Quaid, III |
| 2004/0034283 | A1 | 2/2004 | Quaid, III |
| 2004/0034302 | A1 | 2/2004 | Abovitz et al. |
| 2004/0050394 | A1 | 3/2004 | Jin |
| 2004/0070822 | A1 | 4/2004 | Takayama et al. |
| 2004/0099175 | A1 | 5/2004 | Perrot et al. |
| 2004/0102772 | A1 | 5/2004 | Baxter et al. |
| 2004/0106916 | A1 | 6/2004 | Quaid et al. |
| 2004/0111113 | A1 | 6/2004 | Nakamura et al. |
| 2004/0117032 | A1 | 6/2004 | Roth |
| 2004/0138525 | A1 | 7/2004 | Saadat et al. |
| 2004/0138552 | A1 | 7/2004 | Harel et al. |
| 2004/0140786 | A1 | 7/2004 | Borenstein |
| 2004/0153057 | A1 | 8/2004 | Davison |
| 2004/0173116 | A1 | 9/2004 | Ghorbel et al. |
| 2004/0176664 | A1 | 9/2004 | Iddan |
| 2004/0183777 | A1 | 9/2004 | Bevirt et al. |
| 2004/0215331 | A1 | 10/2004 | Chew et al. |
| 2004/0225229 | A1 | 11/2004 | Viola |
| 2004/0254680 | A1 | 12/2004 | Sunaoshi |
| 2004/0267326 | A1 | 12/2004 | Ocel et al. |
| 2005/0014994 | A1 | 1/2005 | Fowler et al. |
| 2005/0021069 | A1 | 1/2005 | Feuer et al. |
| 2005/0029978 | A1 | 2/2005 | Oleynikov et al. |
| 2005/0043583 | A1 | 2/2005 | Killmann et al. |
| 2005/0049462 | A1 | 3/2005 | Kanazawa |
| 2005/0054901 | A1 | 3/2005 | Yoshino |
| 2005/0054902 | A1 | 3/2005 | Konno |
| 2005/0064378 | A1 | 3/2005 | Toly |
| 2005/0065400 | A1 | 3/2005 | Banik et al. |
| 2005/0083460 | A1 | 4/2005 | Hattori et al. |
| 2005/0095650 | A1 | 5/2005 | Julius et al. |
| 2005/0096502 | A1 | 5/2005 | Khalili |
| 2005/0143644 | A1 | 6/2005 | Gilad et al. |
| 2005/0154376 | A1 | 7/2005 | Riviere et al. |
| 2005/0165449 | A1 | 7/2005 | Cadeddu et al. |
| 2005/0234435 | A1 | 10/2005 | Layer |
| 2005/0283137 | A1 | 12/2005 | Doyle et al. |
| 2005/0288555 | A1 | 12/2005 | Binmoeller |
| 2005/0288665 | A1 | 12/2005 | Woloszko |
| 2006/0020272 | A1 | 1/2006 | Gildenberg |
| 2006/0036264 | A1 | 2/2006 | Selover et al. |
| 2006/0046226 | A1 | 3/2006 | Bergler et al. |
| 2006/0100501 | A1 | 5/2006 | Berkelman et al. |
| 2006/0119304 | A1 | 6/2006 | Farritor et al. |
| 2006/0149135 | A1 | 7/2006 | Paz |
| 2006/0152591 | A1 | 7/2006 | Lin |
| 2006/0155263 | A1 | 7/2006 | Lipow |
| 2006/0195015 | A1 | 8/2006 | Mullick et al. |
| 2006/0196301 | A1 | 9/2006 | Oleynikov et al. |

(56) References Cited

U.S. PATENT DOCUMENTS

2006/0198619 A1 9/2006 Oleynikov et al.
2006/0241570 A1 10/2006 Wilk
2006/0241732 A1 10/2006 Denker et al.
2006/0253109 A1 11/2006 Chu
2006/0258954 A1 11/2006 Timberlake et al.
2007/0032701 A1 2/2007 Fowler et al.
2007/0043397 A1 2/2007 Ocel et al.
2007/0055342 A1 3/2007 Wu et al.
2007/0080658 A1 4/2007 Farritor et al.
2007/0106113 A1 5/2007 Ravo
2007/0123748 A1 5/2007 Meglan
2007/0135803 A1 6/2007 Belson
2007/0142725 A1 6/2007 Hardin et al.
2007/0156019 A1 7/2007 Larkin et al.
2007/0156211 A1 7/2007 Wood et al.
2007/0167955 A1 7/2007 Arnault De La Menardiere et al.
2007/0225633 A1 9/2007 Wood et al.
2007/0225634 A1 9/2007 Wood et al.
2007/0241714 A1 10/2007 Okeynikov et al.
2007/0244520 A1 10/2007 Ferren et al.
2007/0250064 A1 10/2007 Darois et al.
2007/0255273 A1 11/2007 Fernandez et al.
2008/0004634 A1 1/2008 Farritor et al.
2008/0015565 A1 1/2008 Davison
2008/0015566 A1 1/2008 Livneh
2008/0033569 A1 2/2008 Ferren et al.
2008/0045803 A1 2/2008 Williams et al.
2008/0058835 A1 3/2008 Farritor et al.
2008/0058989 A1 3/2008 Oleynikov et al.
2008/0103440 A1 5/2008 Ferren et al.
2008/0109014 A1 5/2008 De La Pena
2008/0111513 A1 5/2008 Farritor et al.
2008/0119870 A1 5/2008 Williams
2008/0132890 A1 6/2008 Woloszko et al.
2008/0161804 A1 7/2008 Rioux et al.
2008/0164079 A1 7/2008 Jacobsen
2008/0183033 A1 7/2008 Bern et al.
2008/0221591 A1 9/2008 Farritor et al.
2008/0269557 A1 10/2008 Marescaux et al.
2008/0269562 A1 10/2008 Marescaux et al.
2009/0012532 A1 1/2009 Blackwell et al.
2009/0020724 A1 1/2009 Paffrath
2009/0024142 A1 1/2009 Ruiz Morales
2009/0048612 A1 2/2009 Farritor et al.
2009/0054909 A1 2/2009 Farritor et al.
2009/0069821 A1 3/2009 Farritor et al.
2009/0076536 A1 3/2009 Rentschler et al.
2009/0137952 A1 5/2009 Ramamurthy et al.
2009/0143787 A9 6/2009 De La Pena
2009/0163929 A1 6/2009 Yeung et al.
2009/0171373 A1 7/2009 Farritor et al.
2009/0234369 A1* 9/2009 Bax ........................ A61B 34/30
606/130
2009/0236400 A1 9/2009 Cole et al.
2009/0240246 A1 9/2009 Deville et al.
2009/0247821 A1 10/2009 Rogers
2009/0248038 A1 10/2009 Blumenkranz et al.
2009/0281377 A1 11/2009 Acosta et al.
2009/0305210 A1 12/2009 Guru et al.
2010/0010294 A1 1/2010 Conlon et al.
2010/0016659 A1 1/2010 Weitzner
2010/0016853 A1 1/2010 Burbank
2010/0042097 A1 2/2010 Newton et al.
2010/0056863 A1 3/2010 Dejima et al.
2010/0069710 A1 3/2010 Yamatani et al.
2010/0069940 A1 3/2010 Miller et al.
2010/0081875 A1 4/2010 Fowler et al.
2010/0139436 A1 6/2010 Kawashima et al.
2010/0185212 A1 7/2010 Sholev
2010/0198231 A1 8/2010 Scott
2010/0204713 A1 8/2010 Ruiz Morales
2010/0245549 A1 9/2010 Allen et al.
2010/0250000 A1 9/2010 Blumenkranz et al.
2010/0262162 A1 10/2010 Omori
2010/0292691 A1 11/2010 Brogna
2010/0318059 A1 12/2010 Farritor et al.
2011/0015569 A1 1/2011 Kirschenman et al.
2011/0020779 A1 1/2011 Hannaford et al.
2011/0071347 A1 3/2011 Rogers et al.
2011/0071544 A1 3/2011 Steger et al.
2011/0077478 A1 3/2011 Freeman et al.
2011/0082365 A1 4/2011 Mcgrogan et al.
2011/0098529 A1 4/2011 Ostrovsky et al.
2011/0152615 A1 6/2011 Schostek et al.
2011/0224605 A1 9/2011 Farritor et al.
2011/0230894 A1 9/2011 Simaan et al.
2011/0237890 A1 9/2011 Farritor et al.
2011/0238080 A1 9/2011 Ranjit et al.
2011/0264078 A1 10/2011 Lipow et al.
2011/0270443 A1 11/2011 Kamiya et al.
2011/0276046 A1 11/2011 Heimbecher et al.
2012/0029277 A1 2/2012 Sholev
2012/0029727 A1 2/2012 Malik
2012/0035582 A1 2/2012 Nelson et al.
2012/0109150 A1 5/2012 Blackwell et al.
2012/0116362 A1 5/2012 Kieturakis
2012/0179168 A1 7/2012 Farritor et al.
2012/0253515 A1 10/2012 Coste-Maniere et al.
2013/0041360 A1 2/2013 Farritor et al.
2013/0053866 A1 2/2013 Leung et al.
2013/0131695 A1 5/2013 Scarfogliero et al.
2013/0345717 A1 12/2013 Markvicka et al.
2014/0039515 A1 2/2014 Mondry et al.
2014/0046340 A1 2/2014 Wilson et al.
2014/0058205 A1 2/2014 Frederick et al.
2014/0100587 A1 4/2014 Farritor et al.
2014/0180308 A1 6/2014 Von Grnberg
2014/0249546 A1 9/2014 Shvartsberg et al.
2014/0276944 A1 9/2014 Farritor et al.
2014/0303434 A1 10/2014 Farritor et al.
2015/0051446 A1 2/2015 Farritor et al.
2015/0297299 A1 10/2015 Yeung et al.
2016/0015461 A1 1/2016 Farritor et al.
2016/0074055 A1 3/2016 Ravikumar et al.
2016/0228154 A1 8/2016 Mickiewicz et al.
2017/0035526 A1 2/2017 Farritor et al.
2017/0354470 A1 12/2017 Farritor et al.
2018/0116734 A1 5/2018 Yeung et al.
2018/0140377 A1 5/2018 Reichenbach et al.
2019/0090965 A1 3/2019 Farritor et al.
2019/0223967 A1 7/2019 Abbott et al.
2020/0046441 A1 2/2020 Liu et al.
2020/0078097 A1 3/2020 Gregerson et al.
2020/0078907 A1 3/2020 Huang
2020/0214775 A1 7/2020 Farritor et al.
2020/0289228 A1 9/2020 Denlinger et al.
2021/0045836 A1 2/2021 Farritor et al.
2021/0369389 A1 12/2021 Parrini et al.
2022/0000569 A1 1/2022 Farritor et al.

FOREIGN PATENT DOCUMENTS

CN 109171977 A 1/2019
CN 114599303 A * 6/2022 ............. A61B 34/37
CN 115227399 A * 10/2022 ............. A61B 90/50
DE 102010040405 A1 3/2012
EP 105656 A2 4/1984
EP 279591 A1 8/1988
EP 1354670 A1 10/2003
EP 2286756 A1 2/2011
EP 2329787 A2 6/2011
EP 2563261 A1 3/2013
EP 2684528 A1 1/2014
EP 2123225 B1 12/2014
EP 2815705 A1 12/2014
EP 2881046 A2 6/2015
EP 2937047 A1 10/2015
JP H04144533 A 5/1992
JP H05115425 A 5/1993
JP H06507809 A 9/1994
JP H06508049 A 9/1994
JP H07016235 A 1/1995
JP H07136173 A 5/1995
JP H07306155 A 11/1995

(56) References Cited

FOREIGN PATENT DOCUMENTS

| | | | |
|---|---|---|---|
| JP | H08224248 | A | 9/1996 |
| JP | 2001505810 | A | 5/2001 |
| JP | 2002000524 | A | 1/2002 |
| JP | 2003220065 | A | 8/2003 |
| JP | 2004180781 | A | 7/2004 |
| JP | 2004322310 | A | 11/2004 |
| JP | 2004329292 | A | 11/2004 |
| JP | 2009106606 | A | 5/2009 |
| JP | 2010533045 | A | 10/2010 |
| JP | 2010536436 | A | 12/2010 |
| JP | 2011504794 | A | 2/2011 |
| JP | 2011045500 | A | 3/2011 |
| JP | 2011115591 | A | 6/2011 |
| JP | 2017509375 | A | 4/2017 |
| KR | 1020150022414 | A | 3/2015 |
| WO | 9221291 | A2 | 12/1992 |
| WO | 0189405 | A1 | 11/2001 |
| WO | 02082979 | A2 | 10/2002 |
| WO | 02100256 | A2 | 12/2002 |
| WO | 2005009211 | A2 | 2/2005 |
| WO | 2005044095 | A1 | 5/2005 |
| WO | 2006005075 | A2 | 1/2006 |
| WO | 2006052927 | A2 | 5/2006 |
| WO | 2006079108 | A1 | 7/2006 |
| WO | 2007011654 | A1 | 1/2007 |
| WO | 2007111571 | A1 | 10/2007 |
| WO | 2007149559 | A2 | 12/2007 |
| WO | 2009023851 | A1 | 2/2009 |
| WO | 2009144729 | A1 | 12/2009 |
| WO | 2010042611 | A1 | 4/2010 |
| WO | 2010046823 | A1 | 4/2010 |
| WO | 2010050771 | A2 | 5/2010 |
| WO | 2011075693 | A1 | 6/2011 |
| WO | 2011118646 | A1 | 9/2011 |
| WO | 2011135503 | A1 | 11/2011 |
| WO | 2013009887 | A1 | 1/2013 |
| WO | 2014011238 | A2 | 1/2014 |
| WO | 2014160086 | A2 | 10/2014 |
| WO | 2015088655 | A1 | 6/2015 |
| WO | 2015132549 | A1 | 9/2015 |

OTHER PUBLICATIONS

Suzumori et al., "Development of Flexible Microactuator and its Applications to Robotics Mechanisms," Proceedings of the IEEE International Conference on Robotics and Automation, 1991: 1622-1627.
Wolfe et al., "Endoscopic Cholecystectomy: An analysis of Complications," Arch. Surg. Oct. 1991; 126: 1192-1196.
Tendick et al. (1993), "Sensing and Manipulation Problems in Endoscopic Surgery: Experiment, Analysis, and Observation," Presence 2(1): 66-81.
Sackier et al., "Robotically assisted laparoscopic surgery," Surgical Endoscopy, 1994; 8: 63-66.
Stiff et al., "Long-term Pain: Less Common After Laparoscopic than Open Cholecystectomy," British Journal of Surgery, 1994; 81: 1368-1370.
Slatkin et al., "The Development of a Robotic Endoscope," Proceedings of the 1995 IEEE International Conference on Robotics and Automation, pp. 162-171, 1995.
Taylor et al., "A Telerobotic Assistant for Laparoscopic Surgery," IEEE Eng Med Biol, 1995; 279-287.
Way et al., (Editors), "Fundamentals of Laparoscopic Surgery," Churchill Livingstone Inc., 1995, 14 pp.
Schippers et al., (1996 "Requirements and Possibilities of Computer-Assisted Endoscopic Surgery," In: Computer Integrated Surgery: Technology and Clinical Applications, pp. 561-565.
Tendick et al., "Applications of Micromechatronics in Minimally Invasive Surgery," IEEE/AS ME Transactions on Mechatronics, 1998; 3(1): 34-42.
Worn et al., "Espirit Project No. 33915: Miniaturised Robot for Micro Manipulation (MINIMAN)" , Nov. 1998; http://www.ipr.ira.ujka.de/-microbot/miniman.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Salky, "What is the Penetration of Endoscopic Techniques into Surgical Practice?" Digestive Surgery, 2000; 17:422-426.
Schurr et al., "Robotics and Telemanipulation Technologies for Endoscopic Surgery," Surgical Endoscopy, 2000; 14: 375-381.
Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.
Yu et al., "Microrobotic Cell Injection," Proceedings of the 2001 IEEE International Conference on Robotics and Automation, May 2001; 620-625.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Feasibility of Robot-Assisted Laparoscopic Surgery," Surgical Laparoscopy, Endoscopy & Percutaneous Techniques, 2002; 12(1 ):41-45.
Ruurda et al., "Robot-Assisted surgical systems: a new era in laparoscopic surgery," Ann R. Coll Surg Engl., 2002; 84: 223-226.
Satava, "Surgical Robotics: The Early Chronicles," Surgical Laparoscopy, Endoscopy & Percutaneous Techniques, 2002; 12(1): 6-16.
Stoianovici et al., "Robotic Tools for Minimally Invasive Urologic Surgery" , Jan. 1, 2002, pp. 1-17.
Thomann et al., "The Design of a new type of Micro Robot for the Intestinal Inspection," Proceedings of the 2002 IEEE Intl. Conference on Intelligent Robots and Systems, Oct. 2002: 1385-1390.
Yu, BSN, RN, "M2ATM Capsule Endoscopy A Breakthrough Diagnostic Tool for Small Intestine Imaging," vol. 25, No. 1, 2002, Gastroenterology Nursing, pp. 24-27.
Riviere et al., "Toward Active Tremor Canceling in Handheld Microsurgical Instruments," IEEE Transactions on Robotics and Automation, Oct. 2003, 19(5): 793-800.
Rentschler et al., Mobile In Vivo Biopsy Robot, IEEE International Conference on Robotics and Automation, Orlando, Florida, May 2006, pp. 4155-4160.
Rentschler et al., "Natural Orifice Surgery with an Endoluminal Mobile Robot," The Society of American Gastrointestinal Endoscopic Surgeons, Dallas, TX, April 2006d, 14 pp.
Sharp LL-151-30, http://www.sharp3d.com, 2006, 2 pp.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Schwartz, "In the Lab: Robots that Slink and Squirm," The New York Times, Mar. 27, 2007, 4 pp.
Roh et al. "Development of the SAIT single-port surgical access robot—slave arm based on RCM Mechanism" 2015 37th Annual International Conference of the IEEE Engineering in Medicine and Biology Society, Aug. 25, 2015, pp. 6.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,106, filed Nov. 26, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,470, filed Nov. 27, 2007.
U.S. Appl. No. 61/025,346, filed Feb. 1, 2008.
Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.

(56) References Cited

OTHER PUBLICATIONS

U.S. Appl. No. 61/030,617, filed Feb. 22, 2008.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Smart Pill "Fastastic Voyage: Smart Pill to Expand Testing," http://www.smartpilldiagnostics.com, Apr. 13, 2005, 1 pg.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Infonnatics—Medicine Meets Virtual Reality, ISO Press, Long Beach, CA, 2005a, III: 397-403.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Sasaki et al., "Forceps Manipulator with Diagonal Joint Mechanism" Proceedings of the 2020 JSME Conference on Robotics and Mechatronics, Japan, The Japan Society of Mechanical Engineers, May 29, 2020, pp. 3, With english abstract.
Mack et al., "Present Role of Thoracoscopy in the Diagnosis and Treatment of Diseases of the Chest," Ann Thorac Surgery, 1992; 54: 403-409.
Peters, "Minimally Invasive Colectomy: Are the Potential Benefits Realized?" Dis Colon Rectum 1993; 36: 751-756.
Liem et al., "Comparison of Conventional Anterior Surgery and Laparoscopic Surgery for Inguinal-hernia Repair," New England Journal of Medicine, 1997; 336 (22): 1541-1547.
Kazemier et al. (1998), "Vascular Injuries During Laparoscopy," J. Am. Coli. Surg. 186(5): 604-5.
Palm, William, "Rapid Prototyping Primer" May 1998 (revised Jul. 30, 2002) (http://www.me.psu.edu/lamancusa/rapidpro/primer/chapter2.htm).
Macfarlane et al., "Force-Feedback Grasper Helps Restore the Sense of Touch in Minimally Invasive Surgery," Journal of Gastrointestinal Surgery, 1999; 3: 278-285.
Li et al. (2000), "Microvascular Anastomoses Performed in Rats Using a Microsurgical Telemanipulator," Comp. Aid. Surg. 5: 326-332.
Meron, "The development of the swallowable video capsule (M2A)," Gastrointestinal Endoscopy 2000; 52 6: 817-819.
Kang et al., "Robotic Assistants Aid Surgeons During Minimally Invasive Procedures," IEEE Engineering in Medicine and Biology, Jan.-Feb. 2001; pp. 94-104.
Lafullarde et al., "Laparoscopic Nissen Fundoplication: Five-year Results and Beyond," Arch/Surg, Feb. 2001; 136: 180-184.
Mack, "Minimally Invasive and Robotic Surgery," JAMA, Feb. 2001; 285(5): 568-572.
Peirs et al., "A miniature manipulator for integration in a self-propelling endoscope," Sensors and Actuators A, 2001, 92: 343-349.
Phee et al., "Development of Microrobotic Devices for Locomotion in the Human Gastrointestinal Tract," International Conference on Computational Intelligence, Robotics and Autonomous Systems (CIRAS 2001), (Nov. 28-30, 2001), Singapore.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Leggett et al. (2002), "Aortic injury during laparoscopic fundoplication," Surg. Endoscopy 16(2): 362.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Phee et al., "Analysis and Development of Locomotion Devices for the Gastrointestinal Tract," IEEE Transaction on Biomedical Engineering, vol. 49, No. 6, Jun. 2002, pp. 613-616.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13 (3):181-184.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Miller, PH.D., et al., "In-Vivo Stereoscopic Imaging System with 5 Degrees-of-Freedom for Minimal Access Surgery," Dept. of Computer Science and Dept. of Surgery, Columbia University, New York, NY, 2004, 7 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, 2004, pp. 239-240.
Kantsevoy et al., "Endoscopic gastrojejunostomy with survival in a porcine model," Gastrointestinal Endoscopy, 2005; 62(2): 287-292.
Menciassi et al., "Shape memory alloy clamping devices of a capsule for monitoring tasks in the gastrointestinal tract," J. Micromech. Microeng, 2005, 15: 2045-2055.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
Park et al., "Experimental studies of transgastric gallbladder surgery: cholecystectomy and cholecystogastric anastomosis (videos)," Gastrointestinal Endoscopy, 2005; 61 (4): 601-606.
Patronik et al., "Preliminary evaluation of a mobile robotic device for navigation and intervention on the beating heart," Computer Aided Surgery, 10(4): 225-232, Jul. 2005.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, 1 Pg.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Kantsevoy et al., "Transgastric endoscopic splenectomy," Surgical Endoscopy, 2006; 20: 522-525.
Ko et al., "Per-Oral transgastric abdominal surgery," Chinese Journal of Digestive Diseases, 2006; 7: 67-70.
Micron, http://www.micron.com, 2006, 1/4-inch VGA NTSC/PAL CMOS Digital Image Sensor, 98 pp.
Rentschler et al., "Mechanical Design of Robotic In Vivo Wheeled Mobility," ASME Journal of Mechanical Design, 2006a, pp. 1-11.
Rentschler et al., "Mobile In Vivo Biopsy and Camera Robot," Studies in Health and Infonnatics Medicine Meets Virtual Reality, vol. 119, pp. 449-454, IOS Press, Long Beach, CA, 2006e.

(56) References Cited

OTHER PUBLICATIONS

Rentschler et al., "Mobile In Vivo Camera Robots Provide Sole Visual Feedback for Abdominal Exploration and Cholecystectomy," Journal of Surgical Endoscopy, 20-1: 135-138, 2006b.
O'Neill, "Surgeon takes new route to gallbladder," The Oregonian, Jun. 2007, 2 pp.
Park et al., "Trocar-less Instrumentation for Laparoscopy: Magnetic Positioning of Intra-abdominal Camera and Retractor," Ann Surg, Mar. 2007; 245(3): 379-384.
Rentschler et al., "An In Vivo Mobile Robot for Surgical Vision and Task Assistance," Journal of Medical Devices, Mar. 2007, vol. 1: 23-29.
Rentschler et al., "In vivo Robotics during the NEEMO 9 Mission," Medicine Meets Virtual Reality, Feb. 17, 2007, 1 pg.
Rentschler et al., "Miniature in vivo Robots for Remote and Harsh Environments," IEEE Transactions on Information Technology in Biomedicine, Jan. 2008; 12(1): 66-75.
Midday Jeff et al., "Material Handling System for Robotic natural Orifice Surgery" , Proceedings of the 2011 Design of medical Devices Conference, Apr. 12-14, 2011, Minneapolis, MN, 4 pages.
In vivo Mobile Surgical Robotic Task Assistance, "1 pg.".
Begos et al., "Laparoscopic Cholecystectomy: From Gimmick to Gold Standard," J Clin Gastroenterol, 1994; 19(4): 625-330.
Fukuda et al., "Mechanism and Swimming Experiment of Micro Mobile Robot in Water," Proceedings of the 1994 EEE International Conference on Robotics and Automation, 1994: 814-819.
Fukuda et al., "Micro Active Catheter System with Multi Degrees of Freedom," Proceedings of the IEEE Intemational Conference on Robotics and Automation, May 1994, pp. 2290-2295.
Hanly et al., "Robotic Abdominal Surgery," The American Journal of Surgery 188 (Suppl.to Oct. 1994): 19S-26S, 2004.
Bailey et al., Complications of Laparoscopic Surgery; Quality Medical Publishers, Inc., 1995, 25 pp.
Green, "Telepresence Surgery", Jan. 1, 1995, Publisher: IEEE Engineering in Medicine and Biology.
Franklin et al., "Prospective Comparison of Open vs. Laparoscopic Colon Surgery for Carcinoma: Five-Year Results," Dis Colon Rectum, 1996; 39: S35-S46.
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Allendorf et al., "Postoperative Immune Function Varies Inversely with the Degree of Surgical Trauma in a Murine Model," Surgical Endoscopy, 1997; 11: 427-430.
Flynn et al., "Tomorrow's Surgery: micromotors and microrobots for minimally invasive procedures," Minimally Invasive Surgery & Allied Technologies, 1998; 7(4): 343-352.
Calafiore et al., Multiple Arterial Conduits Without Cardiopulmonary Bypass: Early Angiographic Results,: Ann Thorac Surg, 1999; 67: 450-456.
Cuschieri, "Technology for Minimal Access Surgery," BMJ, 1999, 319: 1-6.
Faraz et al., "Engineering Approaches to Mechanical and Robotic Design for Minimally Invasive Surgery (MIS)," Kluwer Academic Publishers (Boston), 2000, 13 pp.
Fearing et al., "Wing Transmission for a Micromechanical Flying Insect," Proceedings of the 2000 IEEE International Conference to Robotics &Automation, Apr. 2000; 1509-1516.
Gong et al., Wireless endoscopy, Gastrointestinal Endoscopy 2000; 51(6): 725-729.
Heikkinen et al., "Comparison of laparoscopic and open Nissen fundoplication two years after operation: A prospective randomized trial," Surgical Endoscopy, 2000; 14: 1019-1023.
Ishiyama et al., "Spiral-type Micro-machine for Medical Applications," 2000 International Symposium on Micromechatronics and Human Science, 2000: 65-69.
Abbou et al., "Laparoscopic Radical Prostatectomy with a Remote Controlled Robot," The Journal of Urology, Jun. 2001, 165: 1964-1966.
Bauer et al., "Case Report: Remote Percutaneous Renal Percutaneous Renal Access Using a New Automated Welesurgical Robotic System," Telemedicine Journal and e-Health 2001; (4): 341-347.
Breda et al., "Future developments and perspectives in laparoscopy," Eur. Urology 2001; 40(1): 84-91.
Cavusoglu et al., "Telesurgery and Surgical Simulation: Haptic Interfaces to Real and Virtual Surgical Environments," In McLaughliin, M.L, Hespanha, J.P., and Sukhatme, G., editors. Touch in virtual environments, IMSC Series in Multimedia 2001, 28 pp.
Horgan et al., "Technical Report: Robots in Laparoscopic Surgery," Journal of Laparoendoscopic & Advanced Surgical Techniques, 2001; 11(6): 415-419.
Ballantyne, "Robotic Surgery, Telerobotic Surgery, Telepresence, and Telementoring," Surgical Endoscopy, 2002; 16: 1389-1402.
Cleary et al., "State of the Art in Surgical Robotics: Clinical Applications and Technology Challenges", "Computer Aided Surgery", Jan. 1, 2002, pp. 312-328, vol. 6.
Fraulob et al., "Miniature assistance module for robot-assisted heart surgery," Biomed. Tech. 2002, 47 Suppl. 1, Pt. 1: 12-15.
Guber et al., "Miniaturized Instrument Systems for Minimally Invasive Diagnosis and Therapy," Biomedizinishe Technic. 2002, Band 47, Erganmngsband 1.
Guo et al., "Fish-like Underwater Microrobot with 3 DOF," Proceedings of the 2002 IEEE International Conference on Robotics & Automation, May 2002: 738-743.
Cavusoglu et al., "Robotics for Telesurgery: Second Generation Berkeley/UCSF Laparoscopic Telesurgical Norkstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Dakin et al, "Comparison of laparoscopic skills perfonnance between standard instruments and two surgical robotic s;ystems," Surg Endosc., 2003; 17: 574-579.
Falcone et al., "Robotic Surgery," Clin. Obstel. Gynecol. 2003, 46(1): 37-43.
Fireman et al., "Diagnosing small bowel Crohn's desease with wireless capsule endoscopy," Gut 2003; 52: 39 392.
Franzino, "The Laprotek Surgical System and the Next Generation of Robotics," Surg Clin North Am, 2003 83(6): 1317-1320.
Ang, "Active Tremor Compensation in Handheld Instrument for Microsurgery," Doctoral Dissertation, tech report CMU R.I-TR-04-28, Robotics Institute, Carnegie Mellon University, May 2004, 167 pp.
Breedveld et al., "Design of Steerable Endoscopes to Improve the Visual Perception of Depth During aparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Camarillo et al., "Robotic Technology in Surgery: Past, Present and Future," The American Journal of Surgery, 2004; 188: 2S-15.
Glukhovsky et al., "The development and application of wireless capsule endoscopy," Int. J. Med. Robot. Comput. Assist. Surgery, 2004; I (1): 114-123.
Hanly et al., "Value of the SAGES Learning Center in introducing new technology," Surgical Endoscopy, 2004; 19 (4): 477-483.
Hissink, "Olympus Medical develops capsule camera technology," Dec. 2004, accessed Aug. 29, 2007, http:// www.letsgodigital.org , 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4 pp.
Dumpert et al., "Improving in Vivo Robot Vision Quality," from the Proceedings of Medicine Meets Virtual Reality, ong Beach, CA, Jan. 26-29, 2005. 1 pg.

(56) References Cited

OTHER PUBLICATIONS

Jagannath et al., "Peroral transgastric endoscopic ligation of fallopian tubes with long-term survival in a porcine model," Gastrointestinal Endoscopy, 2005; 61(3): 449-453.
Atmel 80C5X2 Core, http://www.atmel.com, 2006, 186 pp.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Berg et al., "Surgery with Cooperative Robots," Medicine Meets Virtual Reality, Feb. 2007, 1 pg.
Dumpert et al., "Stereoscopic In Vivo Surgical Robots," IEEE Sensors Special Issue on In Vivo Sensors for Medicine, Jan. 2007, 10 pp.
Grady, "Doctors Try New Surgery for Gallbladder Removal," The New York Times, Apr. 20, 2007, 3 pp.
Fuller et al., "Laparoscopic Trocar Injuries: A Report from a U.S. Food and Drug Administration (FDA) Genier for Devices and Radiological Health (CDRH) Systematic Technology Assessment of Medical Products (STAMP) Committee," U.S. Food and Drug Adminstration, available at http://www.fda.gov, Finalized: Nov. 7, 2003; Updated: Jun. 24, 2005, 11 pp.

* cited by examiner

GROSS POSITIONING DEVICE AND RELATED SYSTEMS AND METHODS

CROSS-REFERENCE TO RELATED APPLICATION(S)

This application claims priority to and is a continuation of U.S. patent application Ser. No. 18/482,959, filed Oct. 9, 2023 and entitled "Gross Positioning Device and Related Systems and Methods," which application claims priority to and is a continuation application of U.S. patent application Ser. No. 17/838,883, filed Jun. 13, 2022 and entitled "Gross Positioning Device and Related Systems and Methods," which issued as U.S. Pat. No. 11,813,124 on Nov. 14, 2023, which claims priority to and is a continuation application of U.S. application Ser. No. 15/821,169, filed on Nov. 22, 2017 and entitled "Gross Positioning Device And Related Systems And Methods," which issued as U.S. Pat. No. 11,357, 595 on Jun. 14, 2022, which claims the benefit under 35 U.S.C. § 119 (e) to U.S. Provisional Application 62/425,149, filed Nov. 22, 2016 and entitled "Gross Positioning Device and Related Systems and Methods," the disclosures of each of which are hereby incorporated herein by reference in their entireties.

GOVERNMENT SUPPORT

This invention was made with government support under Grant No. W81XWH-14-1-0058, awarded by the U.S. Department of Defense. The government has certain rights in the invention.

FIELD OF THE INVENTION

The various embodiments herein relate to robotic surgical devices, and more specifically to gross positioning systems and devices that aid in the gross repositioning of surgical devices during surgical procedures. The combination of a gross positioning system with an in vivo surgical device results in an increase in the degrees of freedom of the in vivo device without increasing the size of the device.

BACKGROUND OF THE INVENTION

The known positioning systems currently used for robotic surgery are large and cumbersome. For example, the Da Vinci SP Surgical System™ takes up a significant portion of the operating room and creates a crowded space over the surgical site, and the system created by Waseda University has bulky motor housings that create a larger than necessary profile. In a further example, the Raven™ mimics current laparoscopic techniques by inserting a single tool (in contrast to the in vivo robot systems used in the other two systems discussed above).

FIGS. 1A and 1B depict a known, generic spherical mechanism 10 and the necessary workspace 16 of the mechanism to reach the extents of the abdominal cavity of a patient. A "spherical mechanism" is a physical mechanism or software application that can cause all end effector motions to pass through a single point, thereby allowing a surgical system to use long rigid tools that perform procedures through incisions that serve as single pivot points. As an example, both COBRASurge and the Raven have mechanical spherical mechanisms, while Da Vinci has a software-based spherical mechanism.

This known mechanism as shown in FIGS. 1A and 1B has a cable-driven tool coupled to it. The link angles 12, 14 in the device 10 have been optimized at the University of Washington's BioRobotics lab to create the workspace 16 depicted in FIG. 1B. The workspace 16 is an elliptical cone 90° in the lateral directions and 60° in the cranial/caudal direction with a remote center 18 that is disposed at the bottom of the cone 16. The link angles 12, 14 can be changed for different workspaces.

There is a need in the art for an improved gross positioning system.

BRIEF SUMMARY OF THE INVENTION

Discussed herein are various gross positioning systems for use with in vivo robotic surgical devices.

In Example 1, a gross positioning system for use with a robotic surgical device comprises a base, a first arm link operably coupled to the base at a first rotational joint, a second arm link operably coupled to the first arm link at a second rotational joint, a third arm link operably coupled to the second arm link, and a slidable coupling component slidably coupled to the third arm link such that the slidable coupling component can move along a length of the third arm link between an extended position and a retracted position. The third arm link is rotatable about a third rotational joint and is configured to be positionable through an incision in a patient. The slidable coupling component is configured to be coupleable to the robotic surgical device.

Example 2 relates to the gross positioning system according to Example 1, wherein an axis of rotation of the first rotational joint, an axis of rotation of the second rotational joint, and an axis of rotation of the third rotational joint intersect at a single point of intersection.

Example 3 relates to the gross positioning system according to Example 2, wherein wherein the single point of intersection is a spherical joint.

Example 4 relates to the gross positioning system according to Example 2, wherein the single point of intersection is disposed at some point along a portion of the robotic surgical device.

Example 5 relates to the gross positioning system according to Example 2, wherein the gross positioning system is positioned such that the single point of intersection is disposed at an incision in a patient.

Example 6 relates to the gross positioning system according to Example 5, wherein the third arm link is disposed through the single point of insertion.

Example 7 relates to the gross positioning system according to Example 2, wherein the single point of intersection is disposed at an insertion point of a patient.

Example 8 relates to the gross positioning system according to Example 7, wherein the insertion point comprises an incision or a natural orifice.

Example 9 relates to the gross positioning system according to Example 7, wherein the third arm link is disposed through the single point of intersection.

Example 10 relates to the gross positioning system according to Example 1, wherein the robotic surgical device comprises at least one arm, wherein the gross positioning system and robotic surgical device are configured to operate together to position the robotic surgical device within a body cavity of a patient.

Example 11 relates to the gross positioning system according to Example 10, further comprising a controller operably coupled to the gross positioning system and the robotic surgical device.

In Example 12, a gross positioning system for use with a robotic surgical device comprises a base, a first arm link operably coupled to the base at a first rotational joint, a second arm link operably coupled to the first arm link at a second rotational joint, a third arm link operably coupled to the second arm link at a third rotational joint, a slidable coupling component slidably coupled to the third arm link such that the slidable coupling component can move along a length of the third arm link between an extended position and a retracted position, and the robotic surgical device operably coupled to the slidable coupling component. The robotic surgical device comprises a device body, a first arm operably coupled to the device body, and a second arm operably coupled to the device body. The first arm comprises at least one first actuator and the second arm comprises at least one second actuator.

Example 13 relates to the gross positioning system according to Example 12, wherein an axis of rotation of the first rotational joint, an axis of rotation of the second rotational joint, and an axis of rotation of the third rotational joint intersect at a single point of intersection.

Example 14 relates to the gross positioning system according to Example 12, wherein the third arm link is disposed through the single point of intersection and further is configured to be positionable through an insertion point in a patient.

In Example 15, a external gross positioning system for use with an internal robotic surgical device comprises a base, a first arm link operably coupled to the base at a first rotational joint, a second arm link operably coupled to the first arm link at a second rotational joint, a third arm link operably coupled to the second arm link at a third rotational joint, a slidable coupling component slidably coupled to the third arm link such that the slidable coupling component is moveable along a length of the third arm link between an extended position and a retracted position, and a single point of intersection at an intersection of an axis of rotation of the first rotational joint, an axis of rotation of the second rotational joint, and an axis of rotation of the third rotational joint. The slidable coupling component is configured to be coupleable to the robotic surgical device. The single point of intersection is disposed at an insertion point of a patient.

Example 16 relates to the gross positioning system according to Example 15, wherein a portion of the third arm link is disposed through the single point of intersection.

Example 17 relates to the gross positioning system according to Example 15, wherein a portion of the robotic surgical device is disposed through the single point of intersection.

Example 18 relates to the gross positioning system according to Example 15, wherein the insertion point is an incision.

Example 19 relates to the gross positioning system according to Example 15, wherein the robotic surgical device comprises at least one arm, wherein the gross positioning system and robotic surgical device are configured to operate together to position the robotic surgical device within a body cavity of the patient.

Example 20 relates to the gross positioning system according to Example 19, further comprising a central processing unit operably coupled to the gross positioning system and the robotic surgical device and a controller operably coupled to the central processing unit. The central processing unit comprises software configured to transmit control instructions to the gross positioning system and the robotic surgical device.

In Example 21, a gross positioning system for use with a robotic surgical device comprises a base, a first arm link operably coupled to the base at a first rotational joint, a second arm link operably coupled to the first arm link at a second rotational joint, a third arm link operably coupled to the second arm link at a third rotational joint, a slidable coupling component slidably coupled to the third arm link, and the robotic surgical device operably coupled to the slidable coupling component. Further, the robotic surgical device comprises a device body, a first arm operably coupled to the device body, the first arm comprising at least one first actuator, and a second arm operably coupled to the device body, the second arm comprising at least one second actuator. In addition, the third arm link is positionable through an insertion point in a patient such that the robotic surgical device is positionable within a body cavity of the patient.

Example 22 relates to the gross positioning system according to Example 21, wherein the slidable coupling component is slidable along a length of the third arm link between an extended position and a retracted position.

Example 23 relates to the gross positioning system according to Example 21, wherein an axis of rotation of the first rotational joint, an axis of rotation of the second rotational joint, and an axis of rotation of the third rotational joint intersect at a single point of intersection and the third arm link is disposed through the single point of intersection.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
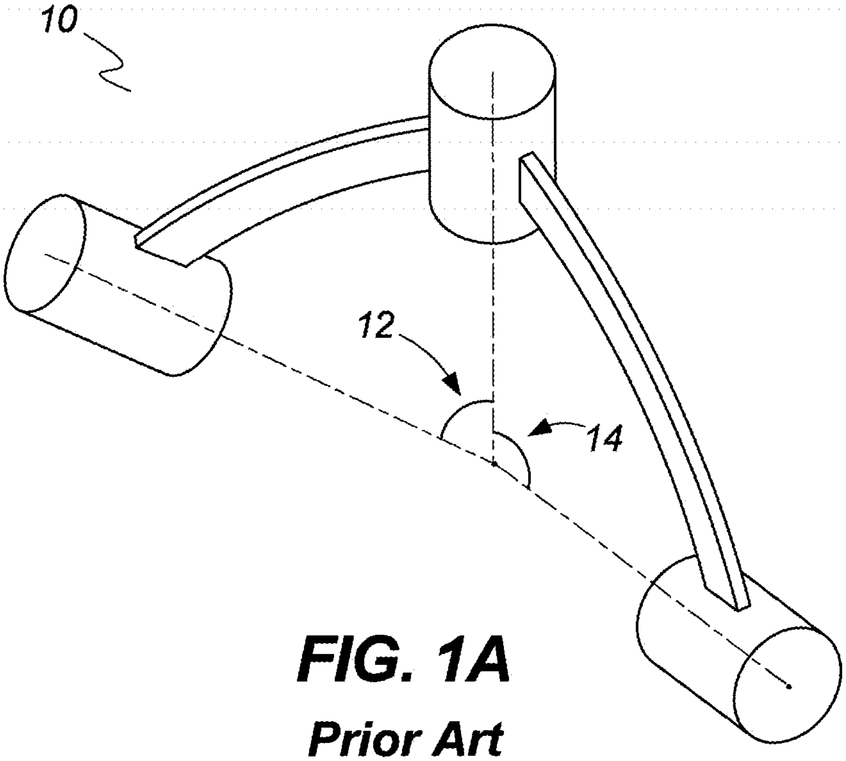
FIG. 1A Prior Art
FIG. 1A is a perspective view of a known spherical mechanism.
Figure 1B:
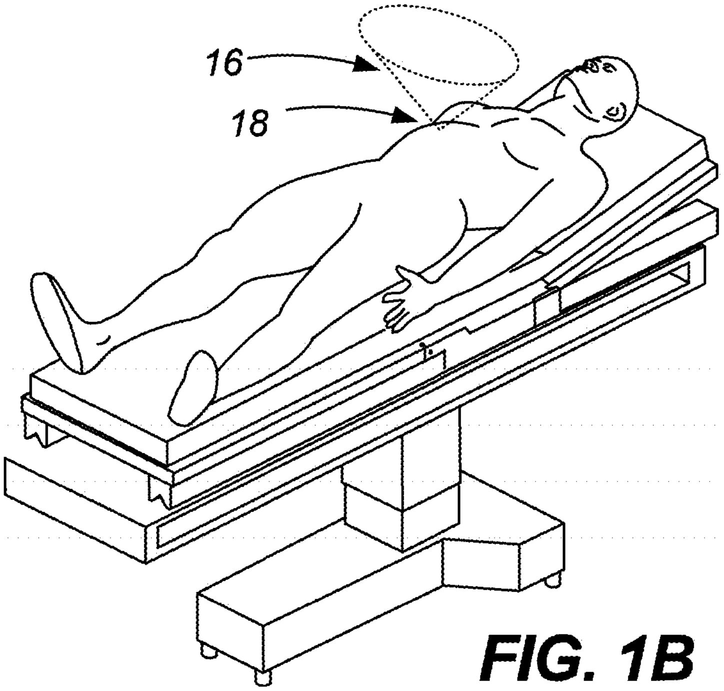
FIG. 1B Prior Art
FIG. 1B is a perspective view of the workspace of the known spherical mechanism of FIG. 1A.

The various embodiments disclosed or contemplated herein relate to an improved gross positioning device that is coupled to a dexterous in vivo robotic device such that the gross positioning device can be used for global orientation of the robotic device within the cavity of a patient as described in further detail herein.

The various gross positioning device implementations disclosed or contemplated herein can be used to automatically grossly position a surgical device inside a cavity of a patient. "Gross positioning," as used herein, is intended to mean general positioning of an entire moveable surgical device (in contrast to precise movement and placement of the specific components of such a device, such as an arm or end effector). In known robotic surgical systems, the gross positioning of those devices during a surgical procedure can be a challenging task. Further, minimally invasive surgical procedures (using either robotic or non-robotic systems) frequently require a surgical technician to reposition the surgical equipment, such as a laparoscope. Such gross repositioning takes time and additional effort. In addition, in some cases, the surgical technician is a junior medical student who is not fully trained in laparoscopy. As a result, the repositioning instructions from the surgeon often result in an obstructed and/or fogged view of the surgical site, requiring additional cognitive resources from the surgeon. Hence, the Da Vinci® system as well as known single incision surgical devices often require timely manual repositioning of the patient, the robotic system, or both while performing complicated procedures.

The various gross positioning devices contemplated herein aid in the gross repositioning of surgical devices (including, for example, any surgical devices that have a device body or rod configured to be positioned through an incision and at least one robotic arm coupled to the device body that is positioned entirely within the cavity of the patient) throughout the procedure without additional intervention or manual repositioning from the surgical staff. The gross positioning system embodiments are capable of controlling the degrees of freedom, azimuth and elevation angle, and roll and translation about the axis of insertion of laparoscopic surgical tools, including robotic laparoscopic surgical tools. As a result, the gross positioning device embodiments disclosed and contemplated herein can grossly position a surgical device through an incision into a patient cavity, such as the abdominal cavity, with high manipulability, reducing the operative time and stress induced upon the surgical staff. The combination of the external gross positioning system with the internal surgical device system will allow the degrees of freedom of the internal system to effectively increase without increasing the size of the surgical robot/device.

In one implementation, the various devices described and contemplated herein can be used with any single site surgical device with an available external positioning fixture, such as a protruding body, rod, or magnetic handle.

Figure 2A:
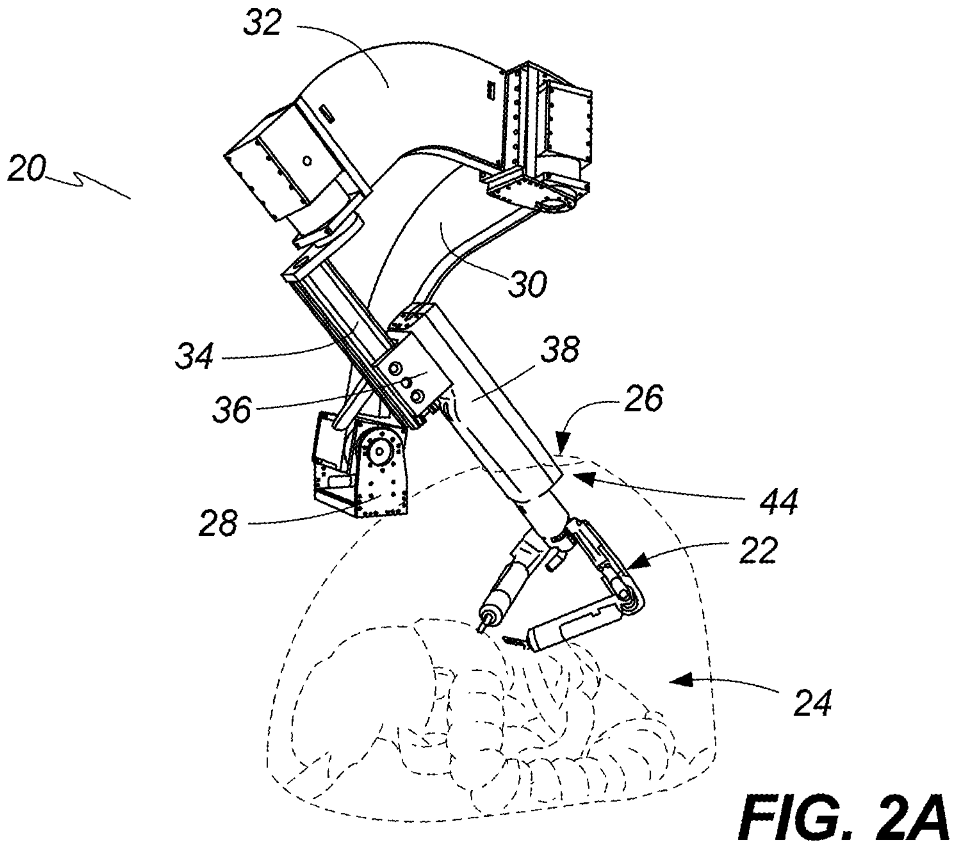
FIG. 2A is a perspective view of a gross positioning device coupled to an in vivo robotic device that is disposed within a cavity of a patient, according to one embodiment.
Figure 2B:
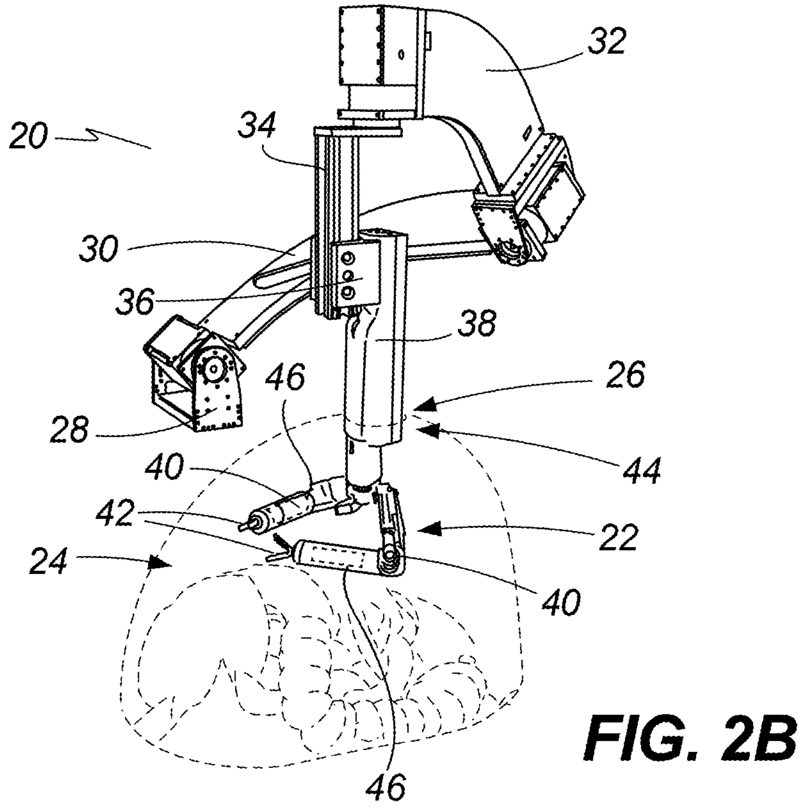
FIG. 2B is another perspective view of the gross positioning device and in vivo robotic device of FIG. 2A disposed within the cavity of the patient.
Figure 2C:
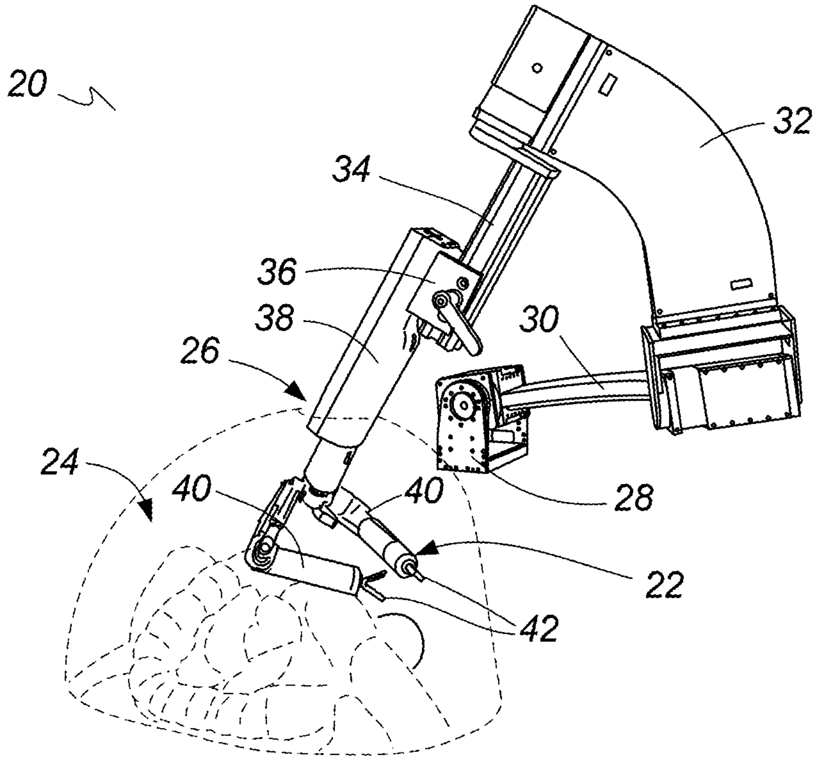
FIG. 2C is another perspective view of the gross positioning device and in vivo robotic device of FIG. 2A disposed within the cavity of the patient.

FIGS. 2A-2C depict a gross positioning device 20 with an in vivo robotic device 22 coupled thereto. The three figures depict the device 20 orienting the robotic device 22 in three different positions within the cavity 24 of the patient through an incision 26. The device 20 has a base (also referred to as a "body") 28, a first arm link (or "upper arm") 30, a second arm link (or "forearm") 32, and a third link (or "extender") 34. The robotic device 22 has a body 38 with two arms 40, with each arm 40 having an actuator 46 and an end effector 42. The extender 34 has a coupling component 36 that couples directly to the body 38 of the robotic device 22 such that the body 38 is disposed through the incision 26 that provides access to the cavity 24 (or, more typically, through a port (not shown) disposed in the incision 26 that provides access to the cavity 24).

As shown, the links 30, 32, 34 of the positioning device 20 (and any other positioning device embodiment disclosed or contemplated herein) allow the robotic device 22 to access the full extent of the workspace within the cavity 24. That is, the positioning device 20 makes it possible to position the robotic device 22 within the patient's cavity 24 with the body 38 of the device 22 positioned through the incision 26 (or port disposed in the incision 26) such that the end effectors 42 attached to the arms 40 of the robotic device 22 can reach any desired location in the workspace in the cavity 24 while the links 30, 32, 34 of the positioning device 20 function to create a "spherical joint" 44 where the device body 38 passes through the incision 26 such that all movements of the robotic device 22 pass through a single point. In other words, regardless of the positioning of the three links 30, 32, 34 and the resulting positioning of the robotic device 22 within the patient's cavity 24, the portion of the device body 38 at the incision 26 (the spherical joint 44) remains in the same position (through the incision 26) as a result of the positioning device 20. This allows operation of a robotic device (such as robotic device 22) within a cavity (such as cavity 24) such that the end effectors (such as end effectors 42) can reach any desired location within the cavity while the entire device 22 is connected to the positioning device 20 via a device body 38 that passes through and never moves from a single point (the spherical joint 44) at the incision 26, thereby making it possible to operate and position the device 22 through that single incision (such as incision 26). The creation of the spherical joint 44 by the positioning device 20 will be described in further detail below. Another advantage is that the positioning device 20 makes it possible to use the single in vivo robotic device within the patient's cavity instead of the multiple arms of the known Da Vinci™ system extending from the patient's cavity and thereby taking up a great deal of workspace outside the body of the patient.

Figure 3:
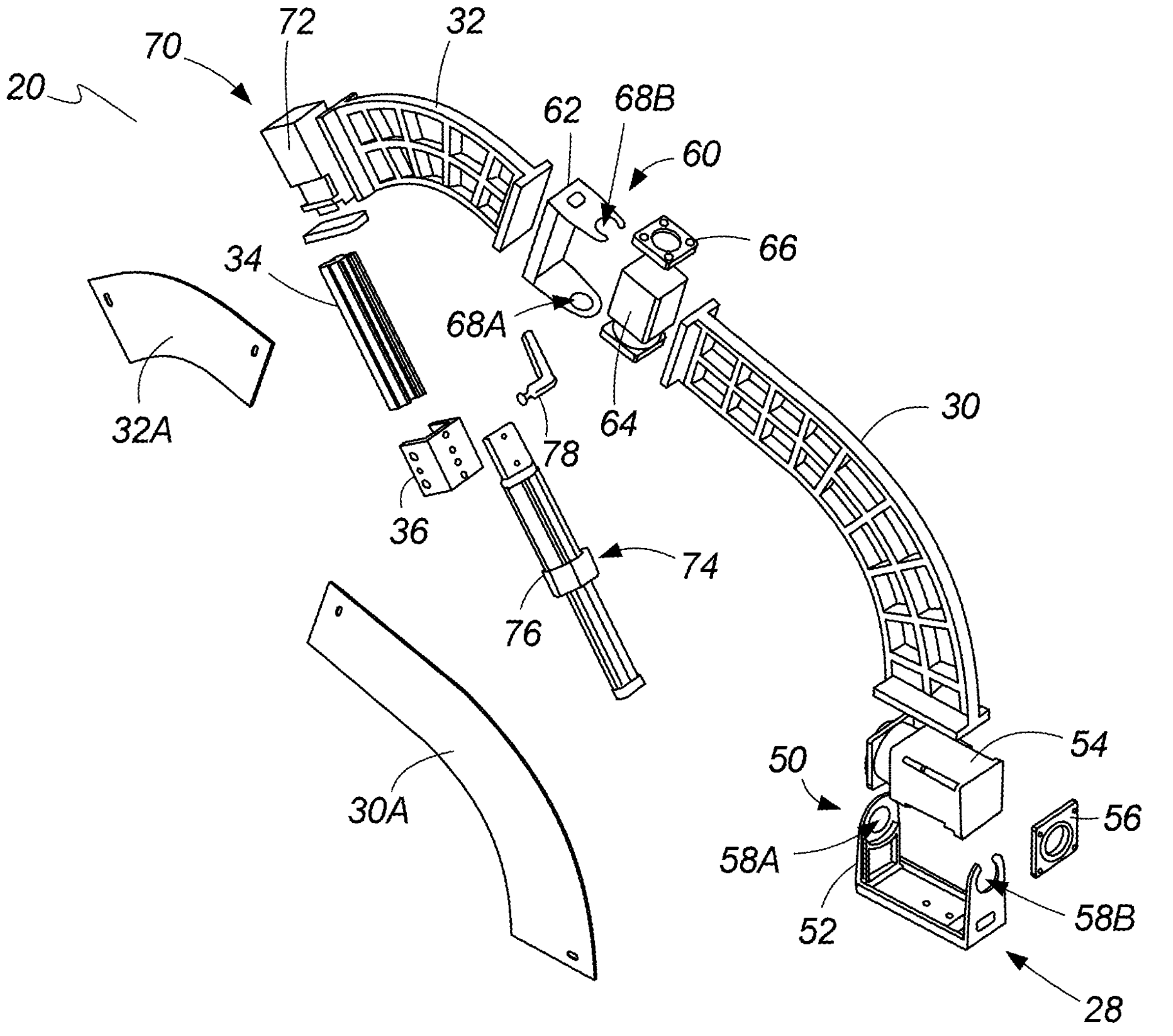
FIG. 3 is an exploded perspective view of a gross positioning device, according to one embodiment.

FIG. 3 depicts an exploded view of the components of the gross positioning device 20. As will be described in further detail below, the device 20 has three degrees of freedom ("DOF") and can utilize those DOFs to provide global orientation for the robotic device 22 (as best shown in FIGS. 2A-2C) coupled to positioning device 20. As discussed above, the device 20 has the base 28, the first arm link 30, the second arm link 32, the third link 34, and the coupling component 36. In this implementation, the first arm link 30 has a cover 30A and the second arm link 32 has a cover 32A. Alternatively, each of the links 30, 32 is a single, unitary component without a cover.

Figure 4:
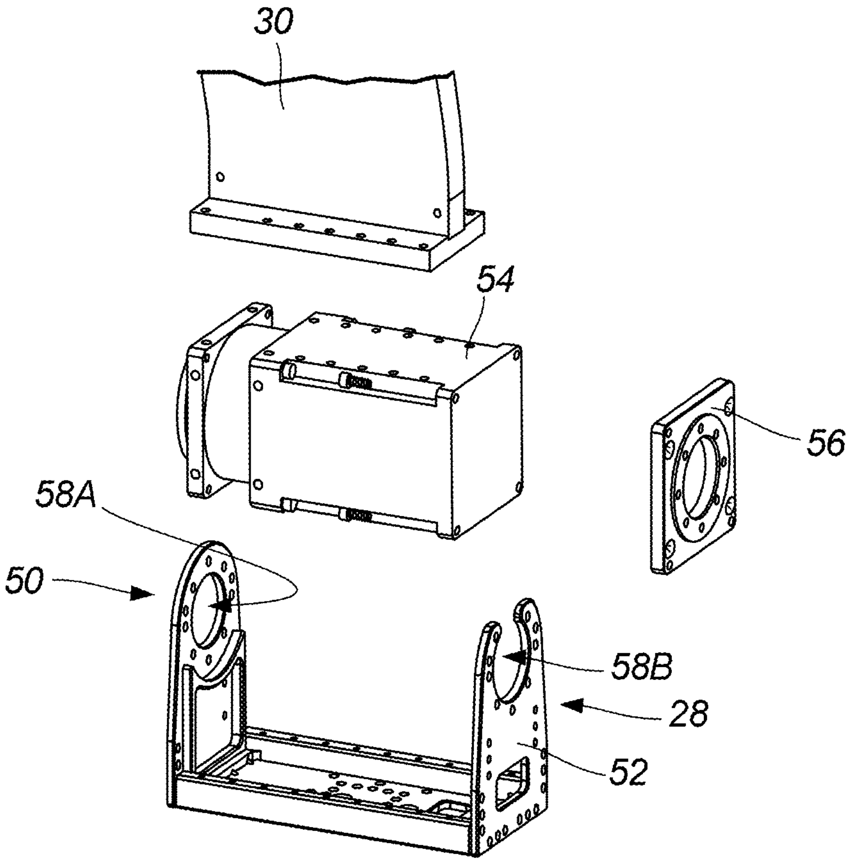
FIG. 4 is an expanded, exploded perspective view of the first joint of the device of FIG. 3.

As best shown in FIGS. 3 and 4, the first arm link 30 is rotatably coupled to the base 28 at a first joint 50. More specifically, the base 28 is made up of a bracket 52 that is configured to receive a first motor 54 that is rotatably coupled to the bracket 52 and a bearing 56, thereby creating the first joint 50. That is, the motor 54 is positioned in the openings 58A, 58B such that the motor 54 rotates within those openings 58A, 58B. The first link 30 is fixedly coupled to the first motor 54 such that actuation of the first motor 54 causes rotation of the motor 54 in relation to the bracket 52, thereby causing rotation of the first link 30 around the first joint 50.

In one implementation, the base 28 is configured to keep the entire device 20 stable and secure during use. As shown, the base 28 is a bracket 52 as discussed above. In alternative embodiments, the base 28 can be any structure that provides such stability, including, for example, a very heavy or weighted structure that uses the weight to enhance stability. In certain implementations, the base 28 can be stably coupled to a surgical table on which the patient is placed. For example, the base 28 can be coupled to a rail (not shown) on the table (not shown). In a further alternative, the base 28 can be coupled to any fixed object in the operating room. Alternatively, the base 28 can be coupled to or be an integral part of a cart or other mobile standalone unit.

Figure 5:
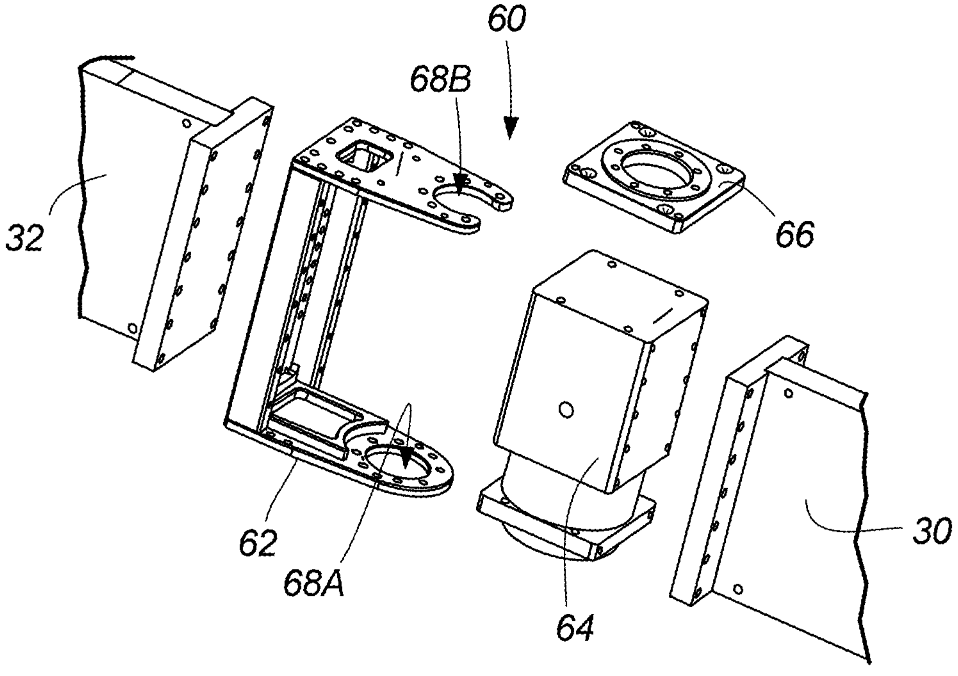
FIG. 5 is an expanded, exploded perspective view of the second joint of the device of FIG. 3.

As best shown in FIGS. 3 and 5, the first arm link 30 and the second arm link 32 are rotatably coupled to each other at a second joint 60. More specifically, the joint 60 is made up of a bracket 62 that is configured to receive a second motor 64 that is rotatably coupled to the bracket 62 and a bearing 66, thereby creating the second joint 60. That is, the motor 64 is positioned in the openings 68A, 68B such that the motor 64 rotates within those openings 68A, 68B. The first link 30 is fixedly coupled to the second motor 64 and the second link 32 is fixed coupled to the bracket 62 such that actuation of the second motor 64 causes rotation of the motor 64 in relation to the bracket 62, thereby causing rotation of the second link 32 in relation to the first link 30 around the joint 60.

Figure 6:
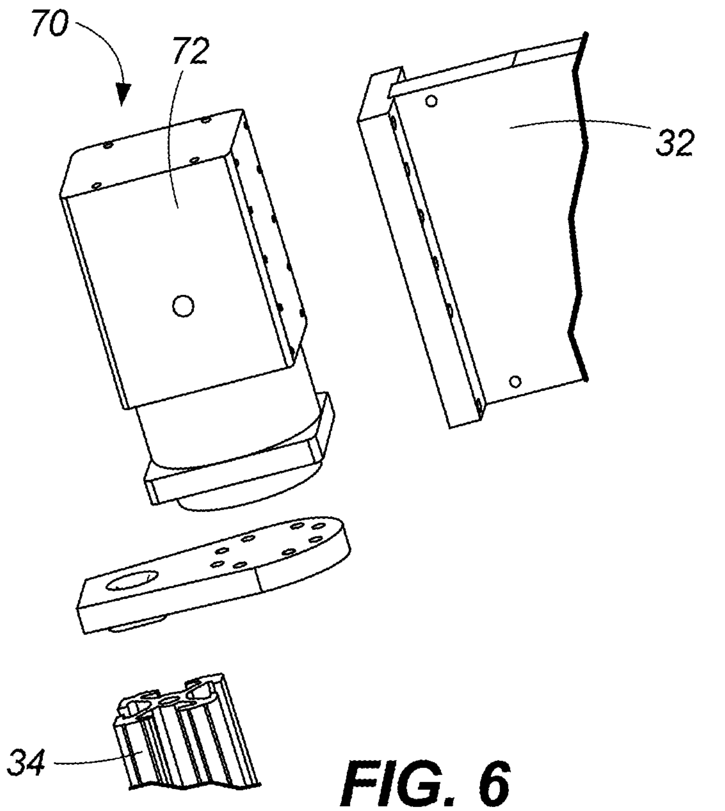
FIG. 6 is an expanded, exploded perspective view of the third joint of the device of FIG. 3.
Figure 7:
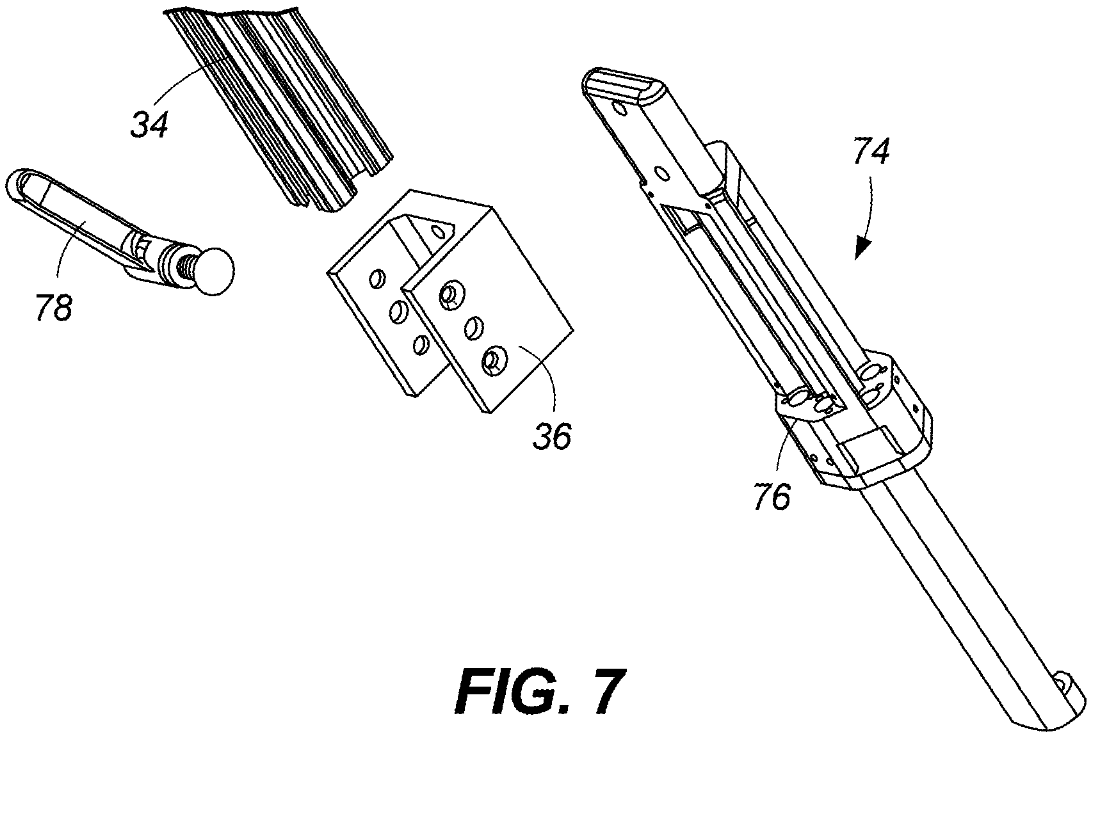
FIG. 7 is an expanded, exploded perspective view of the coupling component of the device of FIG. 3 coupled to a robotic device.

As best shown in FIGS. 3 and 6, the third link 34 is rotatably coupled to the second arm link 32 at a third joint 70. More specifically, the joint 70 is made up of a third motor 72 that is fixedly coupled to the second arm link 32 and rotatably coupled to the third link 34 such that actuation of the motor 72 causes rotation of the third link 34, thereby creating the third joint 70. As best shown in FIGS. 3 and 7, the third link 34 has the coupling component 36 at the distal end of the link 34 such that a robotic device 74 can be coupled thereto. It is understood that the object 74 depicted in FIGS. 3 and 7 is intended to represent an in vivo robotic device 74. In this specific example, only the rod or body 76 of the device 74 is shown, but not the robotic arms or other components. It is understood that this particular body component 76 as shown is merely intended as a schematic depiction of the device 74, and not a fully depiction of an actual robotic device having robotic arms (such as the device 22 discussed and depicted above). Thus, actuation of the third motor 72 causes rotation of the robotic device via the rotation of the third link 34.

Alternatively, any joint configurations can be used in the various gross positioning device implementations, so long as the links 30, 32, 34 can move in relation to each other as described herein.

According to one implementation, the coupling component 36 is slidably coupled to the third link 34 such that the coupling component 36 (and thus the robotic device 74) can be positioned anywhere along the longitudinal length of the third link 34. As such, the robotic device 74 can be moved toward and away from the third joint 70 as desired to position the device 74 along the longitudinal axis of the third link 34. In accordance with certain embodiments, the coupling component 36 has a quick-release handle 78 that can be actuated to fix or unfix the position of the coupling component 36 along the length of the third link 34. That is, the handle 78 can be actuated to move the coupling component 36 into the unfixed configuration such that the component 36 can slide along the length of the link 34. Once the coupling component 36 (and thus the robotic device 74) is positioned at the desired point along the length of the link 34, the handle 78 can be moved into the fixed position, thereby fixing the coupling component 36 at that point such that the component 36 is not slidable. Thus, the coupling component 36 can move along the length of the third link 34 between an extended position and a retracted position and any position therebetween. Alternatively, the third link 34 can have any known component or device that provides for movement between an extended and retracted position.

Figure 8:
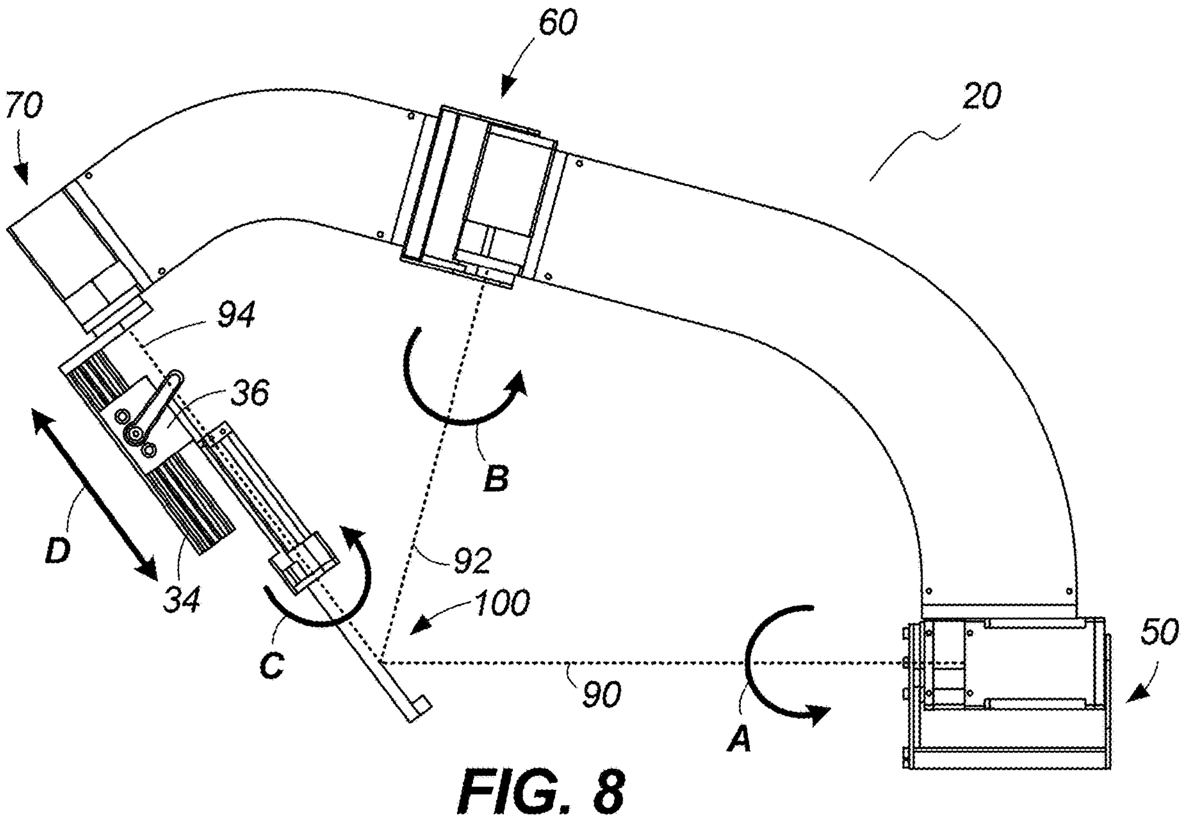
FIG. 8 is a side view of a gross positioning device and the actual axes of rotation resulting at each joint, according to one embodiment.

FIG. 8 depicts the axes of rotation 90, 92, 94 created by the joints 50, 60, 70 and further depict the linear stage D created by the coupling component 36 and third link 34. That is, rotation around axis 90 as shown at arrow A is caused by rotation of the first joint 50. Further, rotation around axis 92 as shown at arrow B is caused by rotation of the second joint 60. Finally, rotation around axis 94 as shown at arrow C is caused by rotation of the third joint 70. In addition, the linear movement represented by the arrow D results from the movement of the coupling component 36 along the third link 34. In one embodiment, the linear movement of the coupling component 36 is utilized at the surgeon's discretion to position the robotic device 74 further into the cavity of the patient (not shown) or to move the robotic device closer to the joint 70. In one implementation, the movement of the coupling component 36 in relation to the third link 34 is manual (and requires actuation of the quick-release lever 78 discussed above). Alternatively, the movement of the coupling component 36 can be motorized.

In one embodiment, the rotational axis 90 at rotational joint 50 is perpendicular to both the rotational axis 92 at rotational joint 60 and the rotational axis 94 at joint 70. In other words, each axis 90, 92, 94 can be perpendicular in relation to the other two. The three axes 90, 92, 94 being perpendicular can, in some implementations, simplify the control of the system 20 by causing each axis 90, 92, 94 to contribute solely to a single degree of freedom. For example, if the third link 34 is rotated around axis 94, the tilt of the in vivo robotic device 74 does not change when all three axes 90, 92, 94 are perpendicular. Similarly, if the first link 30 is rotated around axis 90, only the tilt of the surgical device 74 from side to side is affected. Alternatively, two of the three axes 90, 92, 94 are perpendicular to each other. In a further alternative, none of the axes 90, 92, 94 are perpendicular to each other.

Figure 9:
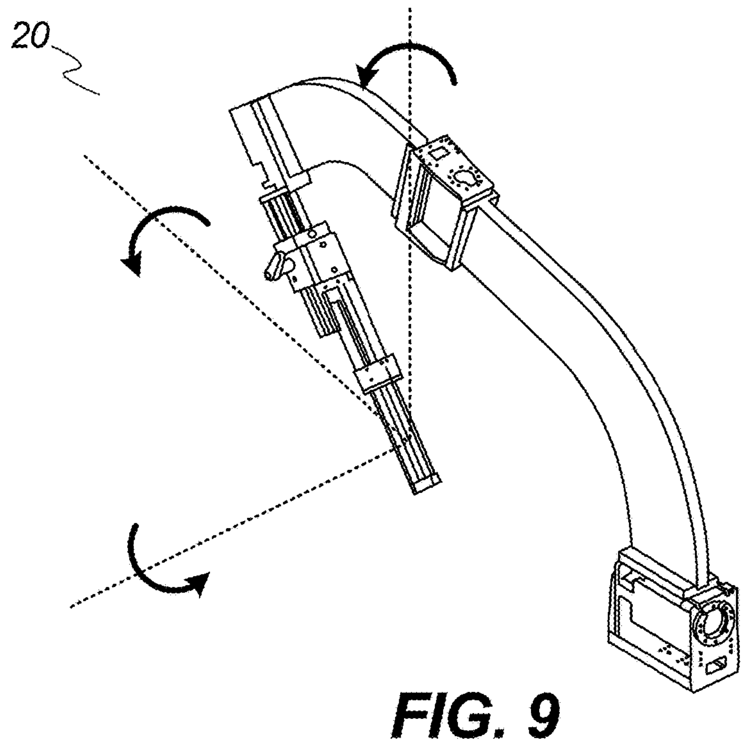
FIG. 9 is a perspective view of the gross positioning device and the global axes of rotation created by the actual axes of rotation of FIG. 8.

FIG. 9 shows how the three local axes of rotation 90, 92, 94 of FIG. 8 result in the global orientation of the in vivo robot 74. That is, FIG. 8 depicts the actual axes of rotation 90, 92, 94 relating to each of the joints 50, 60, 70, respectively. In contrast, FIG. 9 depicts the global axes of rotation 100, 102, 104 that are created by the actual axes of rotation 90, 92, 94. That is, the global axes 100, 102, 104 are the axes used to describe the actual or desired orientation of the robotic device (such as device 74, for example). Thus, the axes 90, 92, 94 create global axis 100 such that rotation around axis 100 as shown at arrow D is the "pitch" rotation of the device 74. Further, the axes 90, 92, 94 create global axis 102 such that rotation around axis 102 as shown at arrow E is the "roll" rotation of the device 74. In addition, the axes 90, 92, 94 create global axis 104 such that rotation around axis 104 as shown at arrow F is the "yaw" rotation of the device 74. As such, according to certain embodiments, a desired global orientation of the device 74 can be controlled by the axes 90, 92, 94. For example, if the pitch of the device 74 is desired to be 90 degrees, then the local axes 90, 92, 94 can be rotated as necessary to some solved value such that the robotic device 74 has a pitch of 90 degrees.

In one embodiment, as best shown in FIG. 8, the three axes 90, 92, 94 intersect at the intersection 100, also known as the "spherical joint" 100 as described above. The intersection 100 remains fixed at the same location, regardless of the positioning of the arm links 30, 32, 34, and can be used as the insertion point during surgeries. That is, the gross positioning system 20 can be positioned such that the intersection 100 is positioned at the incision in the patient through which the robotic device 74 is positioned.

In one implementation, the intersection 100 causes the system 20 to act similarly to a spherical mechanism, as described above. In the device 20 as shown in FIG. 8, the configuration of the device 20 creates the spherical joint 100 such that the extender 34 must pass through the single point of the spherical joint 100, which is typically positioned at the incision in the patient. The spherical joint 100 created by the device 20 increases the size of the effective workspace for the surgical device 74 within the cavity of the patient while maintaining the spherical joint 100 at the incision.

Alternatively, the gross positioning device 20 can have a fourth link, a fifth link, or any number of additional links, and a related additional number of rotational joints. Further, the device 20 can also have fewer than three links, and a related number of rotational joints. In sum, the gross positioning device 20 can have a single rotational joint, two rotational joints, or any number of rotational joints.

Figure 10:
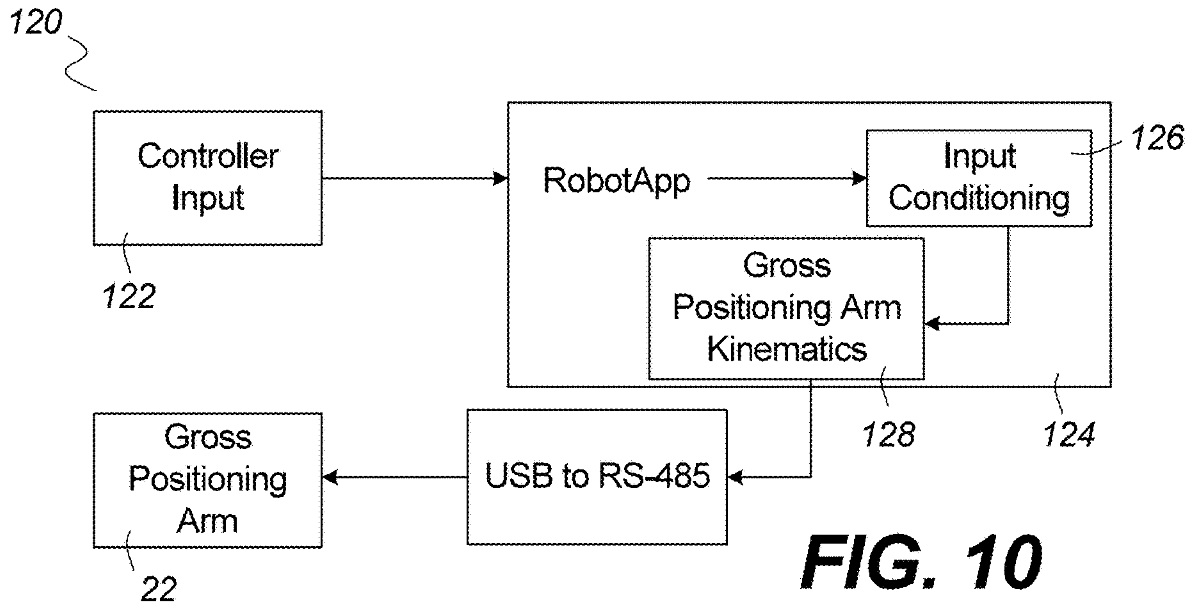
FIG. 10 is a schematic depiction of a control process for controlling a gross positioning device, according to one embodiment.

According to one embodiment, the gross positioning device 20 can be controlled using the following control process 120 as shown in FIG. 10, according to one embodiment. A controller 122 is provided that is used as an input to communicate with the software architecture 124 (informally called the "RobotApp" in this exemplary embodiment). In accordance with one implementation, the software 124 is custom software 124 that allows for the integration of the different hardware and development of "plugins," thereby resulting in a modular platform on which it is easy to build additional features. Alternatively, the software architecture 124 limits the use of hardware to a limited set of hardware and has no modularity. In a further alternative, the software architecture 124 can be any known type of architecture.

The communication from the controller 122 is interpreted (or "conditioned) by the software 124 (block 126) and used to calculate the kinematics (block 128). These kinematic calculations are then communicated to the gross positioning device 20 via a connection 130 such that the device 20 is actuated to move as communicated from the controller 122. In this specific embodiment, the connection is a USB port 130 in the hardware (not shown) that contains the software 124. The port 130 allows for connection of the gross positioning device 20 to the software 124 and thus to the controller 122. In one implementation, the controller 122 is the hardware that contains the software 124. Alternatively, the hardware can be any processing unit, such as a computer.

Figure 11:
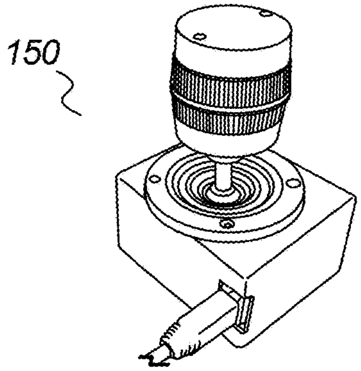
FIG. 11 is a perspective view of a controller, according to one embodiment.
Figure 12:
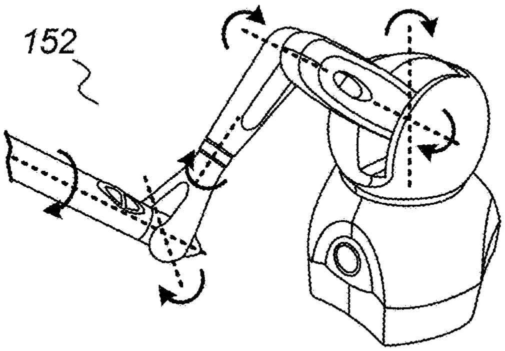
FIG. 12 is a perspective view of another controller, according to a further embodiment.

According to certain embodiments, a hand controller is used to control the gross positioning device and/or the robotic device. In one implementation, the hand controller 150 is a joystick controller 150 as depicted in FIG. 11. The joystick controller 150 controls the orientation of the gross positioning device (such as device 20) A further controller embodiment 152 is depicted in FIG. 12, in which the controller 152 is the commercially available GeoMagic Touch™ controller 152. In this implementation, the controller 152 can be used to control the gross positioning device (such as device 20). In a further embodiment, the controller 152 can be used to control both the gross positioning device (such as device 20) and the robotic device (such as device 22), but the control scheme must be changed each time the user wants to switch from controlling one of the devices to the other.

Figure 13A:
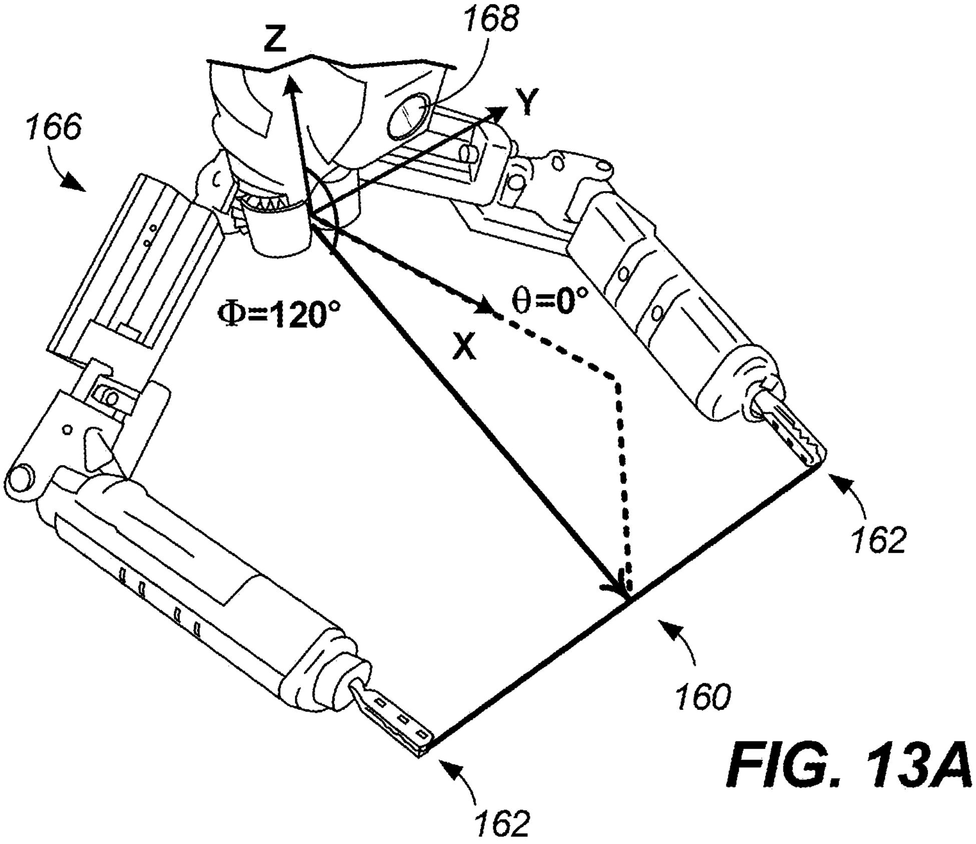
FIG. 13A depicts a perspective view of the arms of robotic device, according to one embodiment.
Figure 13B:
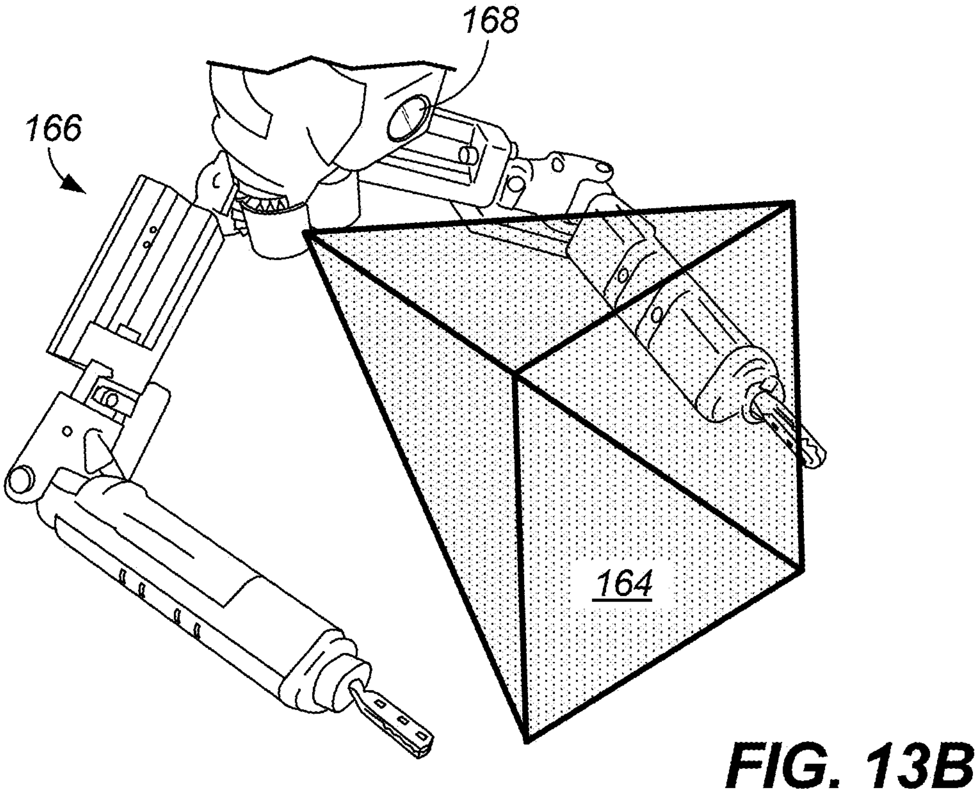
FIG. 13B depicts a perspective view of the arms of the robotic device of FIG. 13A.

In another embodiment, two GeoMagic Touch™ controllers 152 are used in combination with a control process or application that allows for control of both the gross positioning device (such as device 20) and the robotic device (such as device 22) without having to change control schemes during a procedure. Instead, as best shown in FIGS. 13A and 13B, for purposes of the control process, the midpoint 160 between the two endpoints (end effectors) 162 of the in vivo robot 166 was identified. Using polar coordinates (θ, ϕ), a midpoint envelope 164 was developed such that if the midpoint 160 leaves the area of the envelope 164, then the orientation of the in vivo robotic device 166 will be moved accordingly via the gross positioning device (such as device 20). More specifically, if the midpoint 160 of the end effectors 162 reaches the extent of the envelope 164, then the gross positioning device (such as device 20) will begin moving to adjust the view of the camera lens 168 on the device 166. As such, the robotic device 166 can control the view of the camera lens 168 by reaching or "gesturing" up, down, left, or right to move the camera lens 168 to the desired view. In order to stop the movement of the gross positioning device, the end effectors 162 must be returned to the midpoint profile (that is, they must be moved such that the midpoint 160 is within the envelope 164. In this way, the gross positioning device (such as device 20) and the robotic device (such as device 22) can both be operated such that the robotic device can reach the extent of the patient's cavity without changing control schemes.

In one embodiment, the midpoint envelope 164 corresponds to the extent of the camera lens 168. Alternatively, other approaches could be used for different cameras or if the robotic device has an optimal workspace within which it must stay.

Figure 14A:
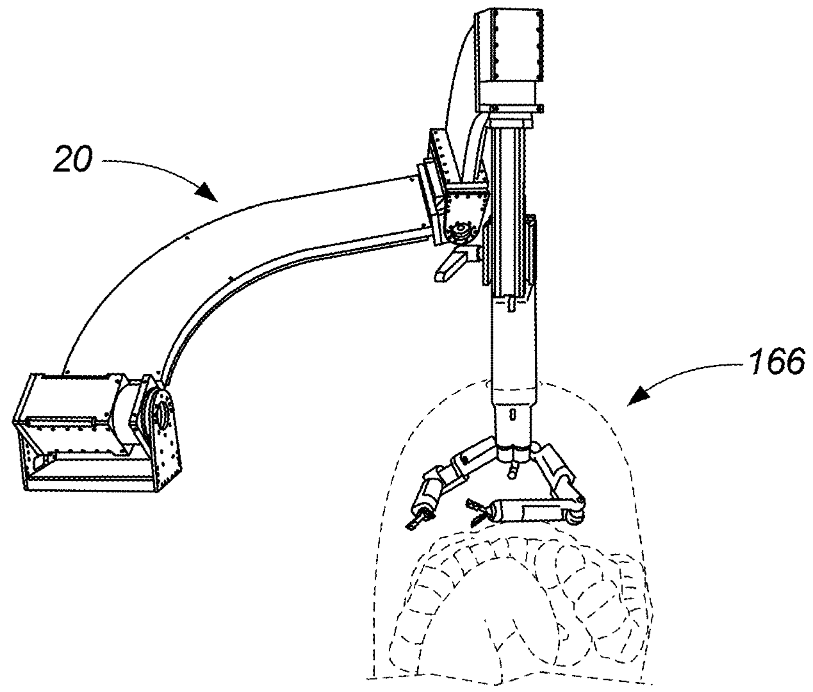
FIG. 14A is a side view of a gross positioning device coupled to an in vivo robotic device that is disposed within a cavity of a patient, according to one embodiment.
Figure 14B:
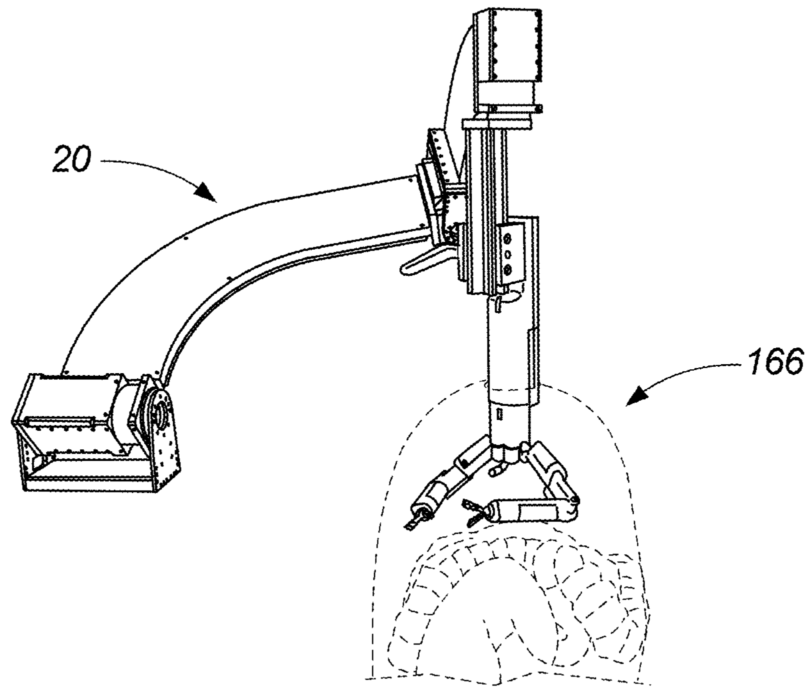
FIG. 14B is another side view of the gross positioning device and in vivo robotic device of FIG. 14A disposed within the cavity of the patient.

Alternatively, the control process can operate in a different fashion, as best shown in FIGS. 14A and 14B. In this particular embodiment, if the midpoint 160 exits the envelope 164, both the gross positioning device (such as device 20) and the in vivo robotic device 166 could move together to keep the end effectors 162 fixed in space but return them inside the midpoint envelope 164 as shown. More specifically, the end effectors 162 are first offset to the right of the robotic device 166, but by repositioning the gross positioning device (such as device 20) and in vivo robot 166 together, the endpoints 162 remain fixed in space, but are returned inside the midpoint envelope 164.

In use, the gross positioning device 20 and other embodiments disclosed or contemplated herein can operate in the following fashion to position the surgical device (such as device 22, device 74, or device 166) within the surgical space in the cavity of the patient through the incision. The three links 30, 32, 34 rotate about the respective axes 90, 92, 94 to position the device 22, 74, 166 as desired. More specifically, the third link 34 can be rotated around axis 94 to rotate the surgical device 22, 74, 166 about the axis 94. Further, the arm links 30, 32 in combination with the extender 34 can be used to articulate the device 20 through two separate angular planes. That is, the two axes 90, 92 can affect the angular position of the extender 34. In addition, the coupling component 36 can be extended or retracted to allow for the surgical device 22, 74, 166 to be advanced into and out of the cavity of the patient.

In one implementation, the positioning system 20 and the surgical device 22, 74, 166 can be used in combination, such that the surgical device 22, 74, 166 is treated as an extension of the positioning system 20 wherein both are used together to move and operate the surgical device 22, 74, 166. For example, the surgeon may want to move the surgical device 22, 74, 166 a total of one inch to the right and thus actuates an external controller to cause this move. The controller (such as any controller embodiment discussed above) transmits the appropriate signals to the positioning system 20 and the surgical device 22, 74, 166 such that the system 20 and device 22, 74, 166 work in combination to move the surgical device 22, 74, 166 one inch to the right. In one example, the system 20 could move 0.5 inches and the device 22, 74, 166 could move 0.5 inches, thereby resulting in the device 22, 74, 166 moving the full one inch as desired. According to one embodiment, the positioning system 20 can thus be used to maximize the strength, workspace, and maneuverability of the combination of the system 20 and the device 22, 74, 166 by determining the optimal contribution of each component during use.

Alternatively, the positioning system 20 and the device 22, 74, 166 operate separately. That is, the system 20 is not operable or does not operate while the device 22, 74, 166 is being used, and the device 22, 74, 166 is not operable or does not operate while the system 20 is being used. For example, if the device 22, 74, 166 is being used and it is determined that a target object in the surgical space is outside the reach of the device 22, 74, 166, the device 22, 74, 166 is "shut down," otherwise rendered inoperable, or simply placed in a "pause mode," and the system 20 is used to reposition the device 22, 74, 166 accordingly.

It is understood that the device 20 can be operably coupled to a processor or computer (not shown) such that the processor can be used to control the positioning system 20, including movement of the arm links 30, 32, 34 to grossly position the surgical device 22, 74, 166.

In a further alternative implementation, the positioning system 20 can also be configured to incorporate or integrate equipment or devices that couple to the surgical device 22, 74, 166 to provide various functionalities to the device 22, 74, 166. For example, in one embodiment, the system 20 can contain suction and irrigation equipment that couples to corresponding equipment in the surgical device 22, 74, 166 such that the surgical device 22, 74, 166 includes suction and irrigation components. In another example according to a further implementation, the positioning device 20 can contain any known equipment that is configured to couple to corresponding equipment in the surgical device 22, 74, 166.

Alternative embodiments contemplated herein also include systems that can be used with surgical devices that are magnetically controlled (in contrast to the surgical devices described above, which are controlled via a body or positioning rod inserted through the surgical incision). In those implementations, the positioning system positions the surgical device anywhere along an internal surface inside the patient's cavity by positioning an external magnetic component (such as a magnetic handle or other type of external magnetic component) along the outer skin of the patient. This positioning of the device can include any combination of movement in two dimensions along the surface of the patient's skin as well as rotation of the external magnetic component about an axis perpendicular to the surface of the skin. Of course, it is understood that while the movement of the magnetic component along the skin of the patient is considered to be two dimensional, the patient's skin is curved such that movement of the external component along the skin demonstrates absolute manipulation in all six degrees of freedom.

Although the present invention has been described with reference to preferred embodiments, persons skilled in the art will recognize that changes may be made in form and detail without departing from the spirit and scope of the invention.

What is claimed is:

1. A gross positioning system for use with a robotic surgical device, the system comprising:

(a) a base;

(b) a first arm link operably coupled to the base at a first rotational joint;

(c) a second arm link operably coupled to the first arm link at a second rotational joint;

(d) a third arm link operably coupled to the second arm link, wherein the third arm link is rotatable about a third rotational joint;

(e) a coupling component coupled to an external portion of the third arm link such that the coupling component is selectively slidable and fixable along a length of the third arm link between an extended position and a retracted position, wherein the coupling component is configured to be coupleable to a device body of the robotic surgical device such that the robotic surgical device is positionable through an incision in a patient; and (f) a controller operably coupled to the gross positioning system and the robotic surgical device.

2. The gross positioning system of claim 1, wherein an axis of rotation of the first rotational joint, an axis of rotation of the second rotational joint, and an axis of rotation of the third rotational joint intersect at a single point of intersection.

3. The gross positioning system of claim 2, wherein the single point of intersection is a spherical joint.

4. The gross positioning system of claim 2, wherein the single point of intersection is disposed at some point along a portion of the robotic surgical device.

5. The gross positioning system of claim 2, wherein the gross positioning system is positioned such that the single point of intersection (100) is disposable at an incision in a patient.

6. The gross positioning system of claim 5, wherein the device body is disposable through the single point of insertion.

7. The gross positioning system of claim 2, wherein the single point of intersection is disposed at an insertion point of a patient.

8. The gross positioning system of claim 7, wherein the insertion point is an incision or a natural orifice.

9. The gross positioning system of claim 7, wherein the device body is disposable through the single point of intersection.

10. The gross positioning system of claim 1, wherein the robotic surgical device further comprises:

(i) a first arm operably coupled to the device body, the first arm comprising at least one first actuator; and (ii) a second arm operably coupled to the device body, the second arm comprising at least one second actuator, wherein the device body is positionable through an insertion point in a patient such that the robotic surgical device is positionable within a body cavity of the patient.

11. The gross positioning system of claim 1, further comprising a single point of intersection of an axis of rotation of the first rotational joint, an axis of rotation of the second rotational joint, and an axis of rotation of the third rotational joint, wherein the single point of intersection is disposable at an insertion point of a patient.

12. The gross positioning system of claim 1, wherein the slidably coupling component is a slidable bracket.

13. The gross positioning system of claim 1, wherein the coupling component comprises a quick-release handle operably coupled to the coupling component, wherein the quick-release handle is selectively actuable to fix or unfix the position of the coupling component in relation to the third arm link.

14. A robotic surgical system for performing surgery on a patient, the system comprising:

(a) a gross positioning device comprising:

(i) a base;

(ii) a first arm link operably coupled to the base at a first rotational joint;

(iii) a second arm link operably coupled to the first arm link at a second rotational joint;

(iv) a third arm link operably coupled to the second arm link, wherein the third arm link is rotatable about a third rotational joint; and (v) a coupling mechanism coupled to the third arm link such that the coupling mechanism is selectively slidable and fixable along a length of the third arm link between an extended position and a retracted position, wherein at least two of an axis of rotation of the first rotational joint, an axis of rotation of the second rotational joint, and an axis of rotation of the third rotational joint substantially intersect at a single point of intersection;

(b) a robotic surgical device removably coupled to the coupling mechanism, the robotic surgical device comprising:

(i) a device body;

(ii) a first arm operably coupled to the device body, the first arm comprising a first actuator; and (iii) a second arm operably coupled to the device body, the second arm comprising a second actuator; and (c) a controller operably coupled to the gross positioning device and the robotic surgical device, the controller comprising first and second hand controllers.

15. The robotic surgical system of claim 14, further comprising (d) a processor operably coupled to the controller, the processor is configured to generate control instructions for the gross positioning device and the robotic surgical device such that the gross positioning device and the robotic surgical device operate together to position the robotic surgical device and the first and second arms within a body cavity of the patient.

16. The robotic surgical system of claim 14, wherein the single point of intersection is disposed at an insertion point of the patient.

17. The robotic surgical system of claim 14, wherein the processor is configured to identify a midpoint between endpoints of the first and second arms and, when the midpoint is positioned outside a predetermined area, to generate the control instructions such that at least one of the gross positioning device and the robotic surgical device operates to move the midpoint back within the predetermined area.

18. A robotic surgical system for performing surgery on a patient, the system comprising:

(a) a gross positioning device comprising:

(i) a base;

(ii) a first arm link operably coupled to the base at a first rotational joint, wherein the first rotational joint comprises a first motor;

(iii) a second arm link operably coupled to the first arm link at a second rotational joint, wherein the first rotational joint comprises a second motor;

(iv) a third arm link operably coupled to the second arm link, wherein the third arm link is rotatable about a third rotational joint, wherein the first rotational joint comprises a third motor; and (v) a coupling mechanism coupled to the third arm link such that the coupling mechanism is selectively slidable and fixable along a length of the third arm link between an extended position and a retracted position;

(b) a robotic surgical device removably coupled to the coupling mechanism, the robotic surgical device comprising:

(i) a device body;

(ii) a first arm operably coupled to the device body, the first arm comprising a first actuator and a first end effector; and (iii) a second arm operably coupled to the device body, the second arm comprising a second actuator and a second end effector;

(c) a controller operably coupled to the gross positioning device and the robotic surgical device, the controller comprising first and second hand controllers; and (d) a processor operably coupled to the controller, the processor is configured to generate control instructions for the gross positioning device and the robotic surgical device such that the gross positioning device and the robotic surgical device operate together to position the robotic surgical device and the first and second arms within a body cavity of the patient.

19. The robotic surgical system of claim 18, wherein the processor is configured to identify a midpoint between the first and second end effectors and, when the midpoint is positioned outside a predetermined area, to generate the control instructions such that at least one of the gross positioning device and the robotic surgical device operates to move the midpoint back within the predetermined area.

* * * * *